United States Patent [19]

Kaneko et al.

[11] Patent Number: 5,305,759
[45] Date of Patent: Apr. 26, 1994

[54] EXAMINED BODY INTERIOR INFORMATION OBSERVING APPARATUS BY USING PHOTO-PULSES CONTROLLING GAINS FOR DEPTHS

[75] Inventors: Mamoru Kaneko; Kuniaki Kami, both of Hachioji; Masakazu Gotanda, Kanagawa; Shuichi Takayam, Hachioji; Ichiro Nakamura, Kokubunji; Kazunari Nakamura; Eiichi Fuse, both of Hachioji; Susumu Takahashi, Kunitachi; Yoshihiro Kosaka, Hachioji; Hiromasa Suzuki, Akishima, all of Japan

[73] Assignee: Olympus Optical Co., Ltd., Tokyo, Japan

[21] Appl. No.: 700,225

[22] Filed: May 14, 1991

[30] Foreign Application Priority Data

| Sep. 26, 1990 [JP] | Japan | 2-258477 |
| Sep. 27, 1990 [JP] | Japan | 2-259913 |
| Sep. 27, 1990 [JP] | Japan | 2-259914 |
| Sep. 27, 1990 [JP] | Japan | 2-259915 |
| Sep. 27, 1990 [JP] | Japan | 2-259916 |
| Nov. 22, 1990 [JP] | Japan | 2-319908 |

[51] Int. Cl.$^5$ ............ A61B 1/00; A61B 6/00
[52] U.S. Cl. ............ 128/665; 128/634; 128/6; 606/2; 607/89; 356/318
[58] Field of Search ............ 128/633, 634, 665, 395, 128/4, 6; 606/2, 3, 4; 356/317, 318; 607/88, 89

[56] References Cited

U.S. PATENT DOCUMENTS

| 4,170,987 | 10/1979 | Anselmo et al. | 128/665 |
| 4,281,645 | 8/1981 | Jobsis | 128/633 |
| 4,556,057 | 12/1985 | Hiruma et al. | 128/665 |
| 4,648,400 | 3/1987 | Schneider et al. | 128/395 |
| 4,705,037 | 11/1987 | Peyman et al. | 128/665 |
| 4,768,513 | 9/1988 | Suzuki | 128/665 |
| 4,773,097 | 9/1988 | Suzaki et al. | 128/665 |
| 4,821,117 | 4/1989 | Sekiguchi | 128/665 |
| 4,856,495 | 8/1989 | Tohjoh et al. | 128/6 |
| 4,889,129 | 12/1989 | Dougherty et al. | 128/665 |
| 5,152,295 | 10/1992 | Kobayashi et al. | 128/665 |

OTHER PUBLICATIONS

"Laser Pulse Tomography Using A Streak Camera", Y. Takiguchi et al, Jul. 1986.

"Applications of the 1-D diffusion approximation to the optics of tissues and tissue phantoms", James L. Karagiannes et al, Applied Optics, vol. 28, No. 12, Jun. 15, 1989.

"Femtosecond optical ranging in biological systems", J. G. Fujimoto et al, Optical Society of America, 1986.

*Primary Examiner*—Kyle L. Howell
*Assistant Examiner*—K. M. Pfaffle
*Attorney, Agent, or Firm*—Armstrong, Westerman, Hattori, McLeland & Naughton

[57] ABSTRACT

A photo-pulse from a photo-pulse generating apparatus is branched, where one branch is radiated to an examined body and the reflected light reflected within the examined body is delayed in time in proportion to the depth from the surface of the examined body and is led to a time-analyzing reflected light measuring apparatus. In this measuring apparatus, the other branched reference photo-pulse or reference signal pulse is input as delayed by the time for which the photo-pulse reflected within the examined body returns and only the reflected light component synchronized with the entering timing of this reference light pulse is analyzed in the time and is detected. By varying the detection sensitivity of this measuring apparatus in response to the depth from the surface of the examined body, the interior can be observed.

50 Claims, 23 Drawing Sheets

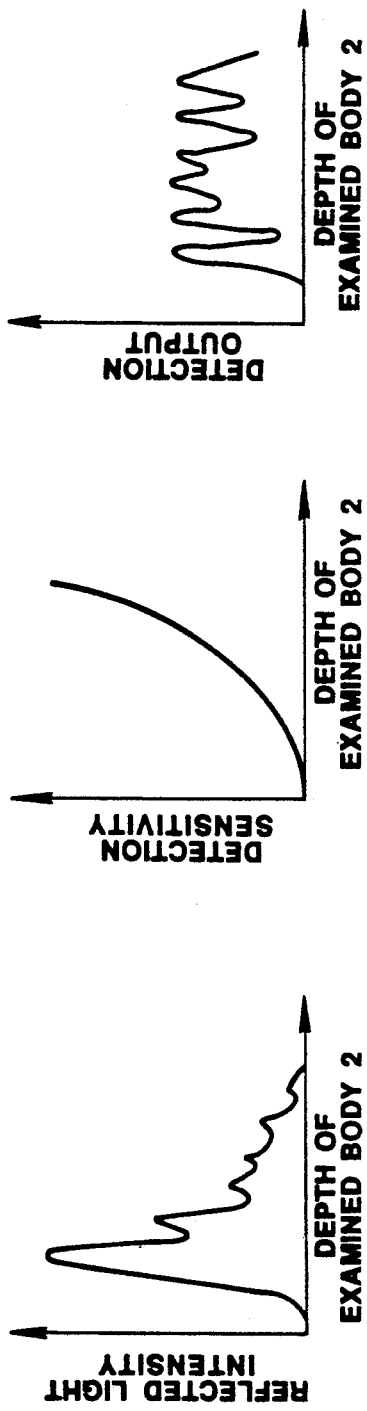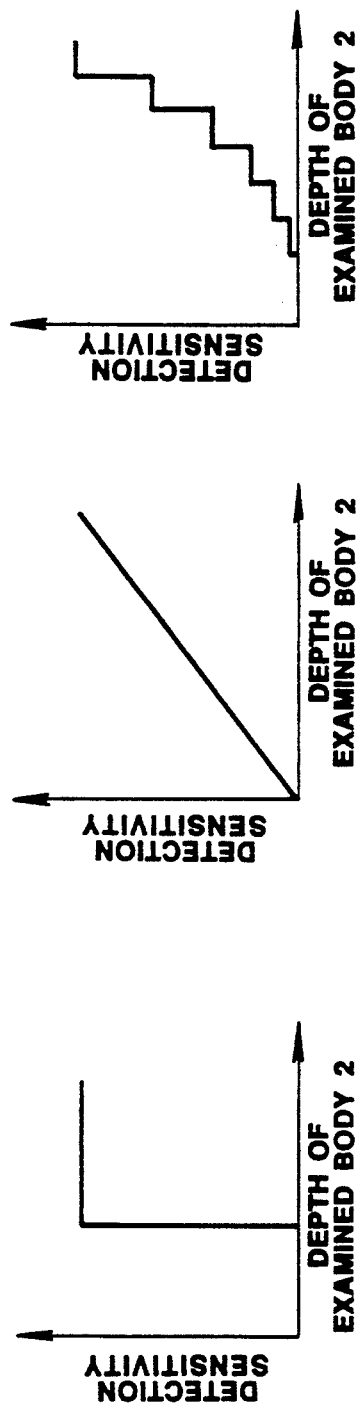

FIG. 14
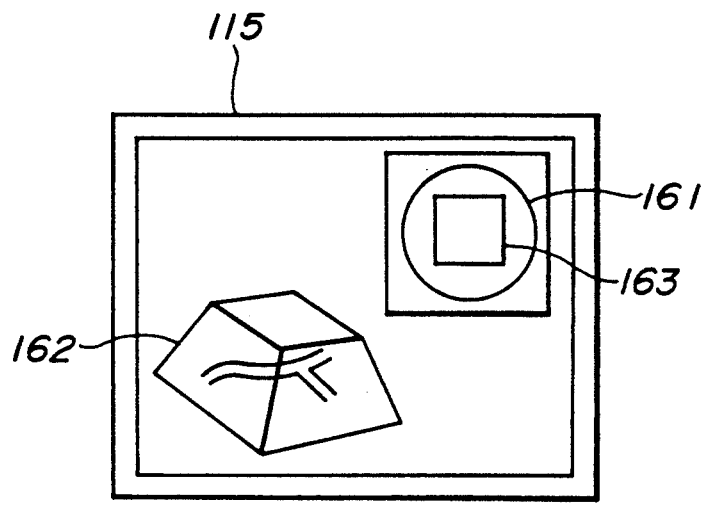
| | | |
|---|---|---|
| FIG. 15a | PULSE LIGHT |  |
| FIG. 15b | RETURNING LIGHT |  |
| FIG. 15c | REFERENCE LIGHT | 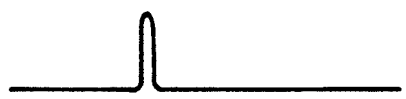 |
| FIG. 15d | SECOND HARMONIC WAVE |  |
| FIG. 15e | REFERENCE LIGHT |  |
| FIG. 15f | SECOND HARMONIC WAVE |  |

FIG.26
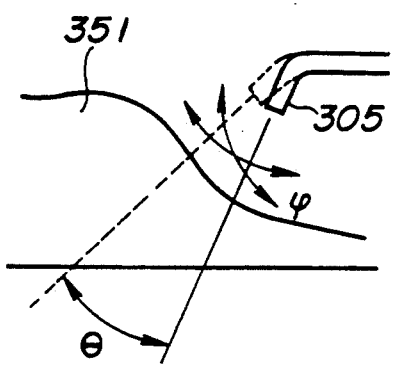
FIG.27a  FIG.27b
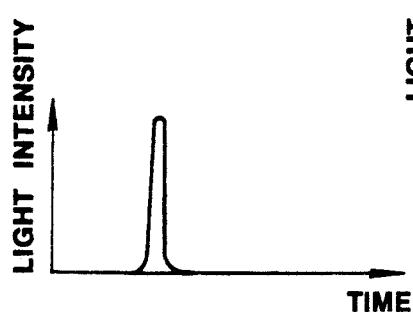
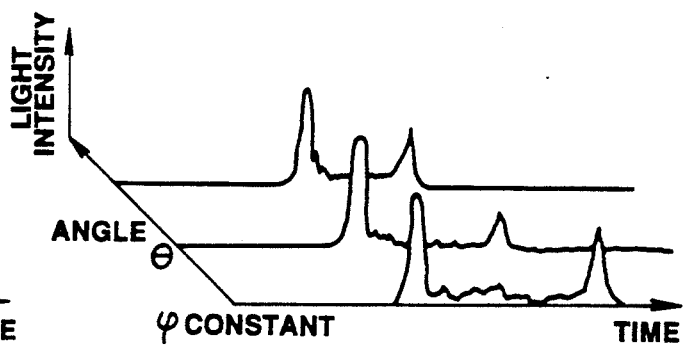
FIG.27c  FIG.27d
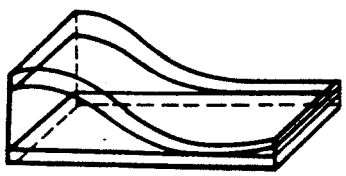

EXAMINED BODY INTERIOR INFORMATION OBSERVING APPARATUS BY USING PHOTO-PULSES CONTROLLING GAINS FOR DEPTHS

BACKGROUND OF THE INVENTION

1. Field of the Invention

This invention relates to an examined body interior information observing apparatus high in sensitivity and favorable in S/N by using photo-pulses for obtaining information of an examined body interior.

2. Description of Related Art

Recently, the importance of vein contrasting has increased along with the increase of circulatory system and brain vein system diseases and the prevalence of the utilization of images in the diagnosis. However, although the vein contrasting has become comparatively easy with the progress of digital radiography, in case it is applied to a human body, the danger and the pain of the examinee should not be neglected.

The information within an examined body such as a living body has been non-invasively measured mostly by X-rays without contact. However, regarding the use of X-rays, there are known problems regarding the influence of radioactive rays and the difficulty of imaging the living body functions. There are also problems in that the apparatus of the NMR-CT method is large and costly and the perspective obtained by ultrasonic waves is low in spatial resolution.

Now, it is known that a hemoglobin (Hb) in blood shows a peculiar spectral variation in response to the oxygenizing degree against the light in the near infrared ray region. By utilizing this feature, as shown, for example, in the article "Living Body Measurement by Using Light" mentioned in the magazine "O plus E", May 1987 to March 1988, the research relating to such non-invasive measurement of living body interior information, such as the blood oxygen saturated degree measurement, are being actively made. It is also shown in the article "Basic Investigation Relating to Visualizing Veins within Living Bodies by Near Infrared Rays" in the Technical Research Report of Electronic Information Communication Society that the hemoglobin (Hb) in blood is so high in the degree of extinction in the infrared ray region than living body tissue as to be able to detect the vein in the tissue as an image by using light.

Aside from the above-mentioned method of observing the interior of a living body from outside the body by using a transmitted light, as shown in the publication of Japanese Patent Application Laid Open No. 85417/1988 and in the article "Femtosecond Optical Ranging in Biological System" in the Optics Letters, Vol. 11, No. 3, 1986, pp. 150 to 152, the interior can be measured also by reflected light. Therein, a light of a pulse width so short as to be of a half value width of several hundred femto- to several pico-second is radiated from a light source to an examined body and the variation over time of the intensity of the reflected light is measured to observe the interior of a living body. In other words, as the lapse of time until the light reflected from a structure at a certain depth from the surface of the living body returns corresponds to the depth, the state of the blood distribution and structure of the living body interior tissue can be measured.

However, it is disclosed in the article "Application of the 1-D diffusion approximation to the optics of tissues and tissue phantoms" in the Appl. Opt., Vol. 28, 1989, pp 2311 to 2317 that near infrared light rays are higher in transmittivity than visible light rays, but the intensity of the transmitted light will attenuate by about 1 to 2 figures even in case the transmitted light passes through a thickness of 1 cm of a muscular tissue, for example, within a living body. In other words, in the above-described method of detecting the reflected light, the deeper in the living body, the lower the intensity of the reflected light due to the absorption and dispersion by the living body tissue and the detected reflected light intensity will no longer correspond to the actual light intensity from the deep part. Also, light intensity from the deeper part will be so low that, with an ordinary detector, the sensitivity will be low and the S/N will be severely attenuated. In such case, it will be considered easy to increase the sensitivity of the detector to detect a feeble signal from the deeper area. However, the strong reflected light from the part near the surface will be simultaneously detected, therefore the signals will be saturated over the allowable detectable range of the detector and, in the worst case, the detector wills seize.

SUMMARY OF THE INVENTION

An object of the present invention is to provide an examined body interior information observing apparatus whereby internal information high in precision and favorable in S/N can be detected without being influenced by the light intensity with the depth of the examined body in the case of detecting the reflected light from deep within such examined body as a living body.

Another object of the present invention is to provide an examined body interior information observing apparatus whereby a measurement at a high sensitivity can be made without seizure of the detector in the case of detecting the reflected light from deep within such examined body.

Another object of the present invention is to provide an examined body interior information observing apparatus whereby cross-sectioned images of the interior of such examined body can be obtained.

An examined body interior information observing apparatus, according to the present invention, comprises a photo-pulse radiating means for radiating photo-pulses for observing the interior of an examined body, a time-analytical detecting means for time-analytically measuring the reflected light radiated by the above-mentioned photo-pulse radiating means and reflected within the examined body in response to the depth of the examined body and at least one of a variable sensitivity means for making variable the detection sensitivity of the above-mentioned time-analytical detecting means in response to the depth of the examined body and a variable positioning means for making variable the position of the lens system so that the reflected light from the observing position may be used to indicate the depth of the observing position of the examined body.

In this formation, whenever the light radiated by the photo-pulse radiating means is reflected within the examined body and this reflected light is detected by the time-analytical detecting means, by using at least one of the variable sensitivity means for making variable the detection sensitivity of the above-mentioned time-analytical detecting means in response to the depth of the examined body, and the variable positioning means for making variable the position of the lens system so that the reflected light from the observing position may be used to indicate the depth of the observing position of the examined body, and internal information of the examined body having a favorable S/N will be able to be detected without being influenced by the light intensity varying with the depth.

BRIEF DESCRIPTION OF THE DRAWINGS

FIGS. 1 to 4 relate to the first embodiment of the present invention.

FIG. 1 is a formation diagram showing the schematic formation of an examined body interior information observing apparatus.

FIG. 2 shows explanatory diagrams showing characteristics by the signal processing of an examined body interior information observing apparatus.

FIG. 3 shows characteristics diagrams showing the sensitivity of a time-analytically measuring apparatus.

FIG. 4 is a concrete formation diagram of the examined body interior information observing apparatus in FIG. 1.

FIG. 7 is a formation diagram showing the scheme of an examined body interior information observing apparatus varying the lens position.

FIG. 8 is an explanatory view showing the measuring principle of the examined body interior information observing apparatus in FIG. 7.

FIG. 9 is a concrete formation diagram of the examined body interior information observing apparatus in FIG. 7.

FIG. 10 is an explanatory diagram relating to a dispersed light suppressing means.

FIG. 11 is an explanatory diagram relating to a dispersed light suppressing means different from than in FIG. 10.

FIGS. 12 to 15 relate to the fourth embodiment of the present invention.

FIG. 12 is an explanatory diagram showing the formation of an operation observing system.

FIG. 13 is an explanatory diagram showing the formation of an optical cross-sectioned image observing apparatus.

FIG. 14 is an explanatory view showing a displayed example of a monitor.

FIG. 15 shows waveform diagrams for explaining the operation of an optical cross-sectioned image observing apparatus.

FIG. 16 is an explanatory view showing the formation of an operation observing system.

FIG. 17 is an explanatory view showing the formation of a rubber scope.

FIG. 18 is a formation diagram of a cross-sectioned image observing photo-scanning apparatus.

FIG. 19 is an explanatory view showing an arrangement of optical fibers.

FIG. 20 is an explanatory view showing a tip form of optical fibers.

FIG. 21 is an explanatory view showing a tip form of optical fibers.

FIG. 22 is a formation diagram of a cross-sectioned image observing photo-scanning apparatus.

FIGS. 23 to 27 relate to the seventh embodiment of the present invention.

FIG. 23 is an explanatory diagram showing the formation of an optical cross-sectioned vein endoscope apparatus.

FIG. 24 is an explanatory diagram showing a scanning driving apparatus.

FIG. 25 is an explanatory diagram showing the formation of an optical cross-sectioned vein endoscope apparatus as being used.

FIG. 26 is an explanatory diagram showing a scanning method for photographing optical cross-sections.

FIG. 27a is a waveform diagram showing an incident photo-pulse.

FIG. 27b is a waveform diagram showing time-analyzed waveforms of a reflected light intensity.

FIG. 27c is an explanatory view showing a cross-section displaying example.

FIG. 27d is an explanatory view showing a three-dimensional displaying example.

FIG. 28 is an explanatory diagram showing the formation of an optical cross-sectioned vein endoscope apparatus.

FIG. 29 is a cross-sectioned view of a tip part of a probe.

FIG. 30 is a characteristics diagram showing the characteristics of the respective filters of an optical cross-sectioned vein endoscope apparatus.

FIG. 32 is a system formation diagram of an optical three-dimensional image observing apparatus.

FIG. 33 is an explanatory view showing an observing example within a body cavity with an optical three-dimensional image observing apparatus.

FIG. 34 is an explanatory view showing the relation between the time of the reflected light and the depth of the tissue.

FIG. 35 is an explanatory diagram showing a time-analyzed waveform of a reflected light intensity.

FIG. 36 is a time chart showing a light switching controlling timing.

FIG. 37 is an explanatory diagram showing measurement results.

FIG. 38 is an explanatory view showing the formation of an endoscope tip for suppressing dispersed lights.

FIG. 39 is an explanatory diagram of a light switching operation by a non-linear optical device.

FIG. 40 is an explanatory view showing an optical fiber bundle for widening the observing region angle.

FIG. 41 is an explanatory view showing a lens array for widening the observing region angle.

FIG. 42 is an elevation of the lens array.

FIG. 43 is an explanatory diagram showing the formation of a rigid electronic endoscope apparatus.

FIG. 44 is an output waveform diagram of a detecting means.

DETAILED DESCRIPTION OF THE PREFERRED EMBODIMENTS

Figure 1:
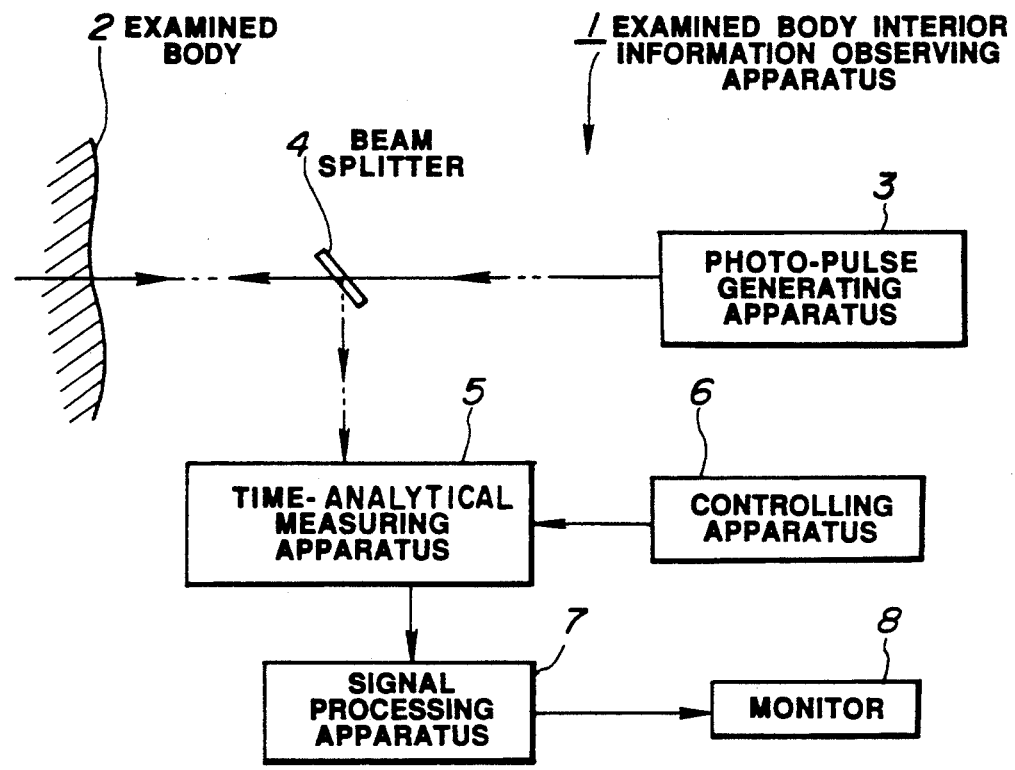

As shown in FIG. 1, an examined body interior information observing apparatus 1 of the first embodiment comprises a photo-pulse generating apparatus 3 for radiating photo-pulses P1 of about several hundred femto to several picoseconds to an examined body 2 which is, for example, a living body, a beam splitter 4 arranged on the optical axis of the photo-pulse generating apparatus 3, a time-analytical measuring apparatus 5 wherein the reflected light from the examined body 2 reflected in the direction at right angles with the above-mentioned optical axis by the beam splitter 4 is time-analyzed and detected and this time analyzed and detected signal is output, a controlling apparatus 6 as a variable sensitivity means for making variable the detection sensitivity of the time-analytical measuring apparatus 5 and a signal processing apparatus 7 for converting the output signal of the time-analytical measuring apparatus 5 to an image signal of the examined body interior information. A monitor 8 displays the internal information of the examined body 2 by the image signal of the above-mentioned signal processing apparatus 7.

The operation of the examined body interior information observing apparatus 1 shall be explained with reference to FIG. 2. (In FIGS. 2a to 2c, the abscissa represents the depth from the surface of the examined body.) The photo-pulse generating apparatus 3 radiates photo-pulses P1 of about several hundred femto to several picoseconds to the examined body 2 through the beam splitter 4. These radiated photo-pulses P1 reflect at respective depths within the body from the surface of the examined body 2 and become a reflected light of superimposed pulse-like lights having respective time differences, as shown in FIG. 2(a). On the other hand, in case the examined body 2 is a living body, the intensity of the light reflecting in response to the depth of the examined body 2 will show characteristics exponentially attenuated with the depth from the surface due to absorption and dispersion by the living body tissue.

This reflected light is reflected by the beam splitter 4 and enters the time-analytical measuring apparatus 5. At this time, the controlling apparatus 6 exponentially increases the detection sensitivity (or amplification rate) of the time-analytical measuring apparatus 5 in response to the depth of the examined body 2, that is, in response to the incident time of the respective reflected lights. Therefore, as shown in FIG. 2(c), the time-analytical measuring apparatus 5 detects a light intensity of a reflected pulse light converted to a substantially constant detected output (light intensity) at any depth of the examined body 2. The signal processing apparatus 7 converts the output signal of the time-analytical measuring apparatus 5 as the internal information of the examined body to an image signal and the monitor 8 displays the internal information of the examined body 2 by the image signal of the above-mentioned signal processing apparatus 7.

In this embodiment, in case the reflected pulse light from deep in the examined body attenuates and is detected without changing the detection sensitivity of the time-analytical measuring apparatus 5, the S/N will deteriorate. Also, in case the detection sensitivity of the time-analyzing measuring apparatus 5 is generally increased, as there is a strong reflected light from the surface of the examined body, the output of the time-analytical measuring apparatus 5 may become saturated and, in the worst case, the apparatus will seize. However, in this embodiment, such will not occur and the internal information favorable in S/N can be detected with a high sensitivity.

FIG. 3 shows examples other than the sensitivity characteristic shown in FIG. 2(b) which may be controlled by the controlling apparatus 6, described as follows:

In FIG. 3(a), a threshold value is provided and is controlled to be on-off is shown so that the reflected pulse light from the surface of the examined body 2 may be suppressed. In FIG. 3(b), the detection sensitivity of the time-analytical measuring apparatus 5 may be made variable in proportion to the depth of the examined body 2. As shown in FIG. 3(c), the detection sensitivity may be variably controlled like steps according to the depth of the examined body.

Figure 4:
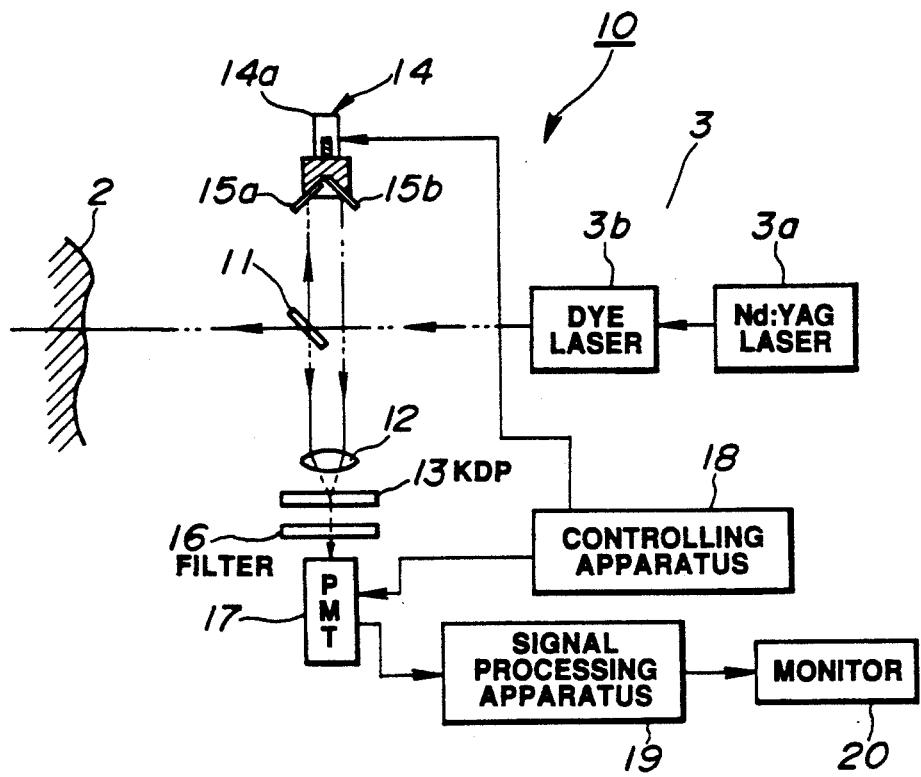

FIG. 4 shows an examined body interior information observing apparatus 10 as an example of this embodiment.

This examined body interior information observing apparatus 10 has as a photo-pulse generating apparatus 3, for example, an Nd:YAG laser 3a which is a solid state semiconductor laser and, for example, a dye laser 3b which is a wavelength variable laser photo-excited to oscillate by a laser light (of a wavelength of 1.06 $\mu$m) and having the wavelength of the laser light variable in a wide range so that a laser light may be emitted as a pulse light of a repeated frequency of 76 MHz and a half value width of about 10 picoseconds. Here, the distance for which a pulse light of about 10 picoseconds proceeds through a living body tissue (of a refractive index of 1.4) is 2.14 mm. That is to say, in case this pulse light is radiated to a living body, it will be able to be measured by a space resolution of 2 to 3 mm. The pulse light from this dye laser 3b is divided by a beam splitter 11 into a radiated light proceeding straight to the examined body 2 and a reference light for taking a detecting timing of a later described time-analytical measuring apparatus.

The straight proceeding light having passed through the beam splitter 11 enters the examined body 2, is reflected by the surface or interior of this examined body 2 and becomes a reflected light which returns to the beam splitter. The light reflected by this beam splitter 11 enters a KDP ($KH_2PO_4$) 13 as a non-linear optical crystal mixing light through a lens 12. In addition, the reference light reflected by the beam splitter 11 and is reflected by delaying mirrors 15a and 15b fitted to a moving stage 14 and enters the KDP 13 through the above-mentioned lens 12.

When the reflected light from the examined body 2 and the above-mentioned reference light enter the above-mentioned KDP 13, a second harmonic wave will be generated. This second harmonic 10 wave passes through an optical filter 16 passing only the second harmonic wave and is detected by a photo-multiplier tube (PMT) 17. When a moving motor 14a driven by the control of a controlling apparatus 18 is rotated and driven, a moving stage 14 will be moved in the optical axis direction to vary the light path length of the delaying mirrors 15a and 15b.

In case the above-mentioned reflected light and reference light are respectively made functions of time, the light intensity of the second harmonic wave generated by the above-mentioned KDP 13 will be proportional to the value obtained by integrating the product of the light intensities of the reflected light and reference light with time. Therefore, when the above-mentioned delaying mirrors 15a and 15b are driven to vary the light path length of the reference light, the intensity of any time component of the reflected light will be able to be detected by the photo-multiplier tube 17. Thus, the time-analyzed waveform of the reflected light from the examined body 2 can be detected. Also, when, for example, an accelerating voltage is variably controlled in response to the above-mentioned light path length by the above-mentioned controlling apparatus 18, the amplification factor of this photo-multiplier tube 17 will be variably controlled.

The above-mentioned examined body interior information observing apparatus 10 is provided with a signal processing apparatus 19 for converting the output signal of the photo-multiplier tube 17 as the internal information of the examined body to an image signal. The monitor 20 displays the internal information of the examined body 2 by the image signal of the above-mentioned signal processing apparatus 19.

In this embodiment, the amplification factor (detection sensitivity) of the photo-multiplier tube 17 is controlled by the controlling apparatus 18 in conformity with the delay amount of the reaching time of the reflected light corresponding to the depth of the reflected light from the examined body 2. Therefore, as shown, for example, in FIGS. 2a to 2c, by elevating the amplification factor of the photo-multiplier tube 17 in conformity with the depth of the examined body 2, the reflected light can be detected and only the strong light from the surface can be intercepted. In case the output signal of the photo-multiplier tube 17 is processed and analyzed and the detection sensitivity is made variable so that the light intensity may be the same, for example, from the surface to the deep of the examined body 2, the comparison of the normal position and abnormal position of the observing position will be made easier and the examined body interior information will be able to be detected with high precision.

Use of such semiconductor device for detecting light as an avalanche photodiode or silicon photodiode other than the photo-multiplier tube 17, the amplification factor of an amplifier provided, for example, in the later step of such device may be made variable. Also, such solid state laser as a semiconductor laser or titanium sapphire (Ti:Al$_2$O$_3$) may be used instead of the dye laser 3b.

Figure 5:
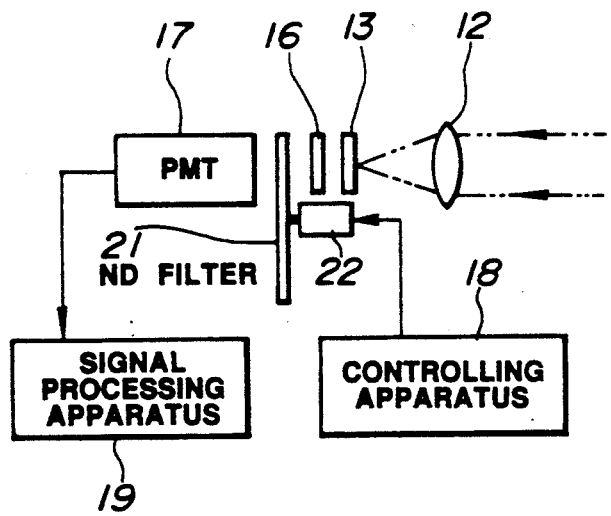
FIG. 5 is a formation diagram showing a modification of the first embodiment.

FIG. 5 is a formation diagram showing a modification of the first embodiment.

In this modification, instead of the system of making variable the amplification factor of the photo-multiplier tube 17, by a rotary variable neutral density (mentioned as variable ND) filter 21, the light intensity of the entering reflected light is made variable and, as a result, the detection sensitivity of the photo-multiplier tube 17 is made variable. The other formations and operations are the same as in the first embodiment, shall bear the same reference numerals and shall not be explained here.

The above-mentioned variable ND filter 21 is arranged between the above-mentioned optical filter 16 and photo-multiplier tube 17 and is rotated and driven by a motor 22 controlled by a controlling apparatus 18.

In this modification, the variable ND filter 21 is provided with a transmittivity distributing filter whereby the light transmittivity in the rotating direction of the motor 22 varies, for example, to be 1% to 100% and, by making variable the rotation angle of the variable ND filter 21 in response to the depth of the examined body 2, the detection sensitivity of the photo-multiplier tube 17 can be varied. The filter characteristic of the variable ND filter 21 may be to provide a 100% transmitting region and a perfect shielded region.

The position of the variable ND filter 21 is not limited to the entire surface of the photo-multiplier tube 17, but may be located on the front surface of the optical filter 16, KDP 13 or lens 12.

The other formations, operations and effects are the same as in the first embodiment and shall not be explained here.

Figure 6:
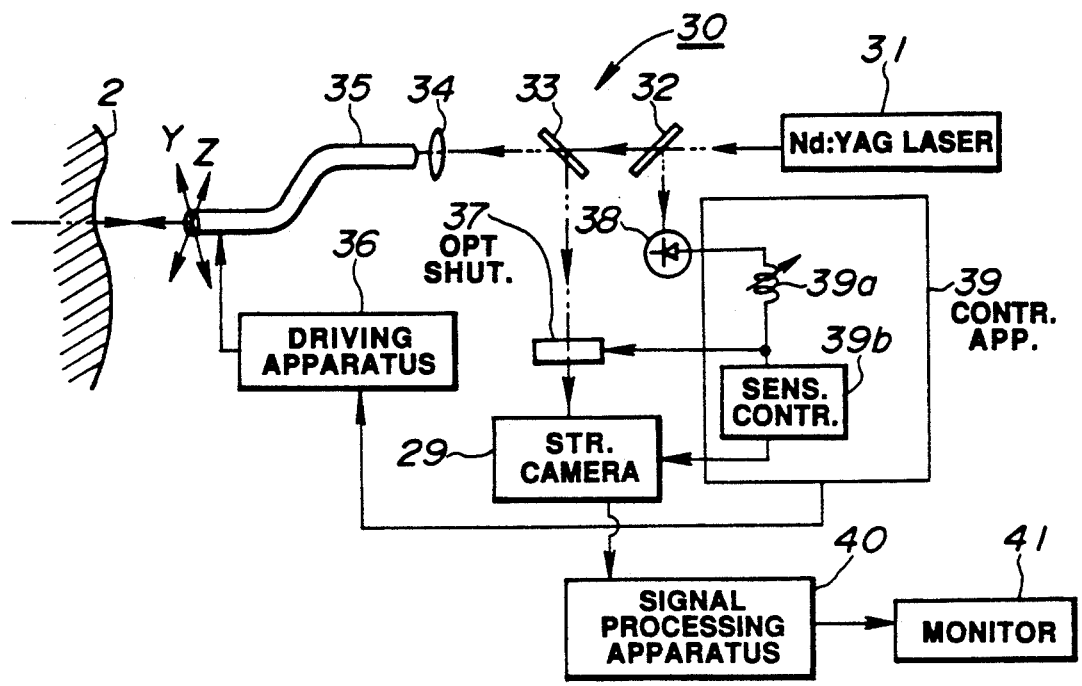
FIG. 6 is a formation diagram relating to the second embodiment of the present invention.
Figure 7:
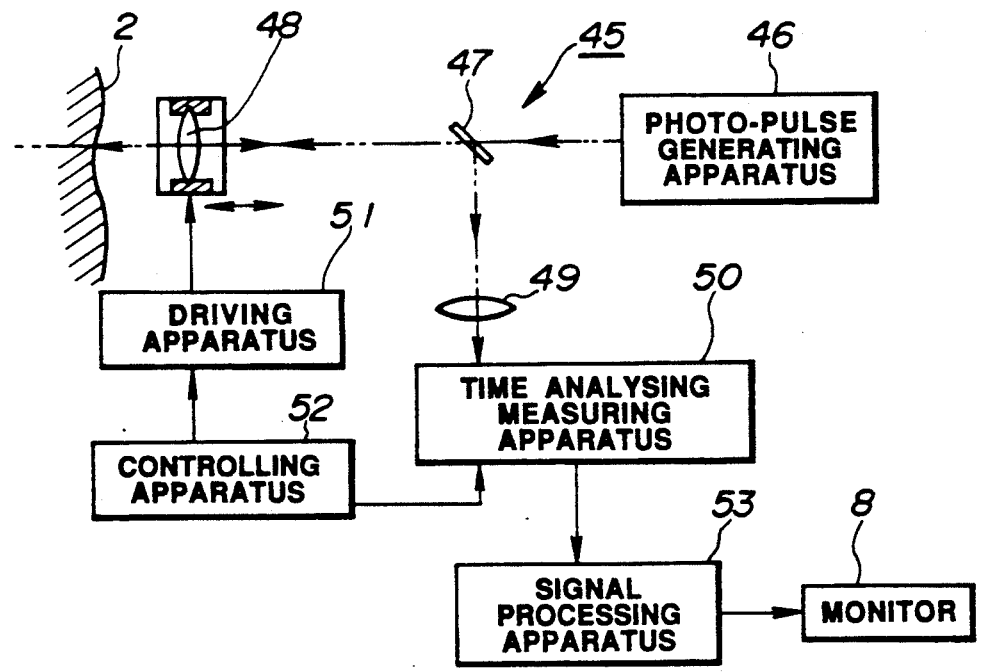
FIGS. 7 to 11 relate to the third embodiment of the present invention.

FIG. 6 is a formation diagram relating to the second embodiment of the present invention.

In this embodiment, a streak camera 29 is provided as a time-analytical detecting means and the radiated light scans the examined body 2 to obtain a cross-sectioned image of the examined body 2. The same formations as in the first embodiment shall bear the same reference numerals and shall not be explained here.

This examined body interior information observing apparatus 30 has an Nd:YAG laser 31 oscillating pulse laser lights. The pulse laser light from the Nd:YAG laser 31 becomes a radiated light proceeding straight to the examined body 2 through a first beam splitter 32 and second beam splitter 33, is condensed by a lens 34 and enters an optical fiber bundle 35. On the other hand, the first beam splitter 32 divides the pulse light into a reference light taking an opening and closing timing of a later described photo-shutter 37 and a measurement starting timing of the above-mentioned streak camera 29.

The above-mentioned optical fiber bundle 35 is made movable in the Y and Z directions (two-dimensional directions) shown in FIG. 6 by a driving apparatus 36. The radiated light having passed through the optical fiber bundle 35 scans the examined body 2. The scanning radiated light is reflected by the examined body 2, returns as a reflected light to the second beam splitter 33, is reflected by the splitter and enters the above-mentioned steak camera 29 through such optical shutter 37 as, for example, a Kerr shutter.

On the other hand, the reference light split by the first beam splitter 32 is converted to an electric signal by a photodiode 38 and is output to a controlling apparatus 39 as a Variable means for opening and closing the above-mentioned photo-shutter 36 and controlling the above-mentioned streak camera 29 and driving apparatus 36. This controlling apparatus 39 can vary the delay amount through a delaying device which can vary the delay amount of a delaying line 39a or the like provided, for example, with a tap as an electric delaying means for electrically delaying electric signal pulses photoelectrically converted by the photodiode 38. By making a control varying this delay amount (as by switching the selecting tap with a switch), only when a very strong reflected light from the examined body surface reaches, the photo-shutter 37 will be closed to prevent the streak camera 29 from seizing. Also, this controlling apparatus 39 can control the detection sensitivity to vary in response to the streak time of the above-mentioned streak camera 29.

By the above-mentioned streak camera 29, when the entering (reflected) light is converted to an electron beam by a cathode electrode and this electron beam is passed between deflecting plates to which a voltage varying with the time is applied, if the time of the entering light is different, the light emitting position (from the case of an applied voltage of 0) on an anode painted with a fluorescence will be different and the reflected light will be able to be detected time-analytically by the displacement of this light emitting position.

When such photoelectric converting device as a two-dimensional CCD is arranged on the above-mentioned fluorescent plate, the reflected light separated with the time will be able to be detected. In case a reflected light component reflected at any depth is extracted from the reflected light from the examined body, the controlling apparatus 39 will make variable the voltage between the cathode and anode in response to the depth and, for example, the larger the depth, the larger the voltage, position displacement, emitted light amount and detection sensitivity.

For example, an electric signal pulse passed through the delaying line 39a is waveform shaped in a waveform shaping circuit not illustrated to control the photo-shutter 37 to open and close and is passed through the detection sensitivity controlling circuit 39b to control the detection sensitivity of the streak camera 29. This detection sensitivity controlling circuit 39b can be formed of a voltage amplifying amplifier or the like in which, with the lapse of time, the output voltage will become higher.

The signal corresponding to the reflected light detected time-analytically by the above-mentioned streak camera 29 is output to a signal processing part 40 consisting of a computer or the like and the signal processing part 40 analyzes and processes the signal on the basis of the detected signal and outputs the cross-sectioned image of the examined body 2 as a signal to a monitor 41 which displays the cross-sectioned image of the internal information of the examined body 2. The controlling apparatus 39 may process the signal part to be the larger the displacement, the higher the amplification factor in the signal processing part 40 instead of varying the voltage between the cathode and anode of the above-mentioned streak camera 29 with the lapse of time.

In this formation, the pulse laser light from the Nd:YAG laser 31 is radiated to the examined body 2 through the first beam splitter 32, second beam splitter 33, lens 34 and optical fiber bundle 35. The optical fiber bundle 35 is driven two-dimensionally by the driving apparatus 36 and the radiated light emitted from the optical fiber bundle 35 scans the examined body 2. The scanning radiated light becomes a reflected light having a time delay in response to the respective depths of the examined body 2, returns to the second beam splitter 33, is reflected by the splitter and enters the above-mentioned streak camera 29 through the photo-shutter 37.

At this time, as the photo-shutter 37 controlled to open and close by the controlling apparatus 39 is closed, the reflected light reflected by the surface of the examined body 2 and having a strong light intensity will be shielded. When the photo-shutter 37 opens at the timing when the following light reflected within the examined body 2 arrives and the detection sensitivity of the streak camera 29 is gradually, for example, exponentially increased in response to the depth of the examined body 2, the reflected light from the depths of the examined body 2 will be also time-analytically detected as a signal having a satisfactorily high S/N. The signal processing part 40 analyzes and processes the signal with a computer on the basis of the detected signal of the streak camera 29 and outputs the cross-sectioned image of the examined body 2 as a signal to the monitor 41 which displays the cross-sectioned image of the internal information of the examined body 2.

In this embodiment, as the controlling apparatus 39 closes the photo-shutter 37 at a time when the reflected light reflected by the surface of the examined body 2 and having a strong light intensity arrives, releases the photo-shutter 37 at a time when the following light reflected within the examined body 2 arrives and can make variable the detection sensitivity of the streak camera 29, the reflected light from the depths of the examined body will be also time-analytically detected as a signal high in the S/N. On the other hand, as the optical fiber bundle 35 is moved by the driving apparatus 36 to radiate the scanning light, a clear cross-sectioned image can be obtained. The other formations, operations and effects are the same as in the first embodiment and shall not be explained here. The third embodiment shall be explained in the following with reference to FIGS. 7 to 11.

This embodiment is an examined body interior information observing apparatus wherein the position of the lens system is made variable so that only the reflected light in response to the depth of a specific examined body 2 may be better detected whereas, in the first and second embodiments, the detection sensitivity of the time-analytical detecting means is made variable in response to the depth of the examined body 2.

An examined body interior information observing apparatus 45 comprises a photo-pulse generating apparatus 46 as a light radiating means for radiating photo-pulses of about several hundred femto to several picoseconds to an examined body 2, a beam splitter 47 arranged on the optical axis of the photo-pulse generating apparatus 45, a condensing lens 48 forming a lens system by which the reflected light made when the radiated light straight proceeding through the beam splitter 47 is reflected by the examined body 2 is made a parallel light, a time-analytical measuring apparatus 50 as a time-analytical measuring means arranged in a position at right angles with the beam splitter 47 on the above-mentioned optical axis and entered by the reflected light from the examined body returning through the condensing lens 48 and beam splitter 47, a driving apparatus 51 as a movable means for moving the above-mentioned condensing lens 48 forward and rearward in the above-mentioned optical axis direction and elevating the reflected light detecting efficiency, a controlling apparatus 52 for making variable at any time the detecting timing of the above-mentioned time-analytical measuring apparatus 50 and driving and controlling the driving apparatus 51 and a signal processing apparatus 53 for converting the output signal of the time-analytical measuring apparatus 50 as the examined body interior information to an image signal.

A monitor 8 displays the internal information of the examined body 2 by the image signal of the above-mentioned signal processing apparatus 53.

The operation of the examined body interior information observing apparatus 45 of this embodiment shall be explained.

The photo-pulse generating apparatus 46 radiates photo-pulses of about several hundred femto to several picoseconds to the examined body 2 through the beam splitter 47 and condensing lens 48. This radiated light is reflected at respective depths within the body from the surface of the examined body 2 as a reflected light in which pulse lights having respective time differences are superposed. On the other hand, the radiated pulse lights from the photo-pulse generating apparatus 46 arrive spot-like to be squeezed in to enter the condensing lens 48.

Figure 8:
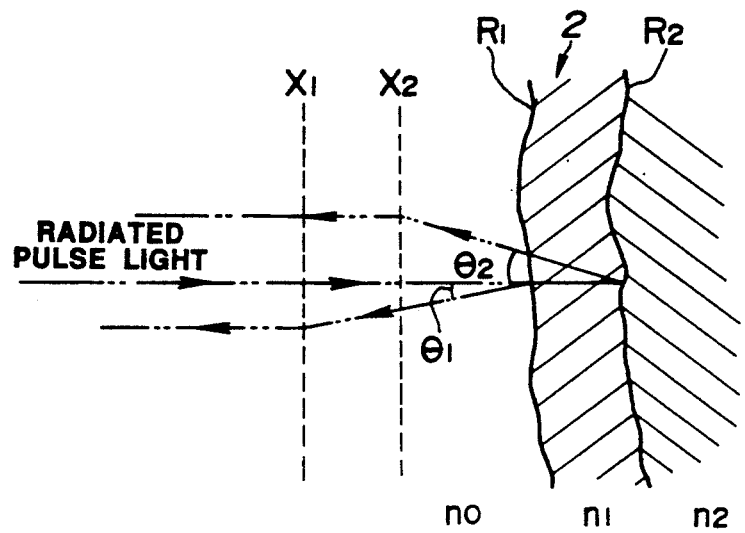

Here, as shown in FIG. 8, the radiated pulse light from the photo-pulse generating apparatus is reflected by the boundary surface R1 (refractive index n1) of the examined body 2 from air (refractive index n0) and its reflection angle is $\theta1$. As it is, the reflected light of the reflection angle of $\theta1$ cannot be detected but, for example, in case the condensing lens 48 is positioned in x1, the reflected light will be made a parallel light by the condensing lens 48 and will be detected by the time-analytical measuring apparatus 50.

Also, the radiated pulse light is reflected by the boundary surface R2 (refractive index n2) and its reflection angle is $\theta2$. As it is, the reflected light of the reflection angle of $\theta2$ cannot be detected but, for example, in case the condensing lens 48 is positioned in x2, the reflected light will be made a parallel light by the condensing lens 48 and will be detected by the time-analytical measuring apparatus 50. Therefore, in case the light reflected by the boundary surface R1 or R2 or the light reflected at any depth of the examined body 2 is to be detected, as the reflected light can be made a parallel light by making variable the position of the condensing lens 48, at the focal distance of the condensing lens 48, the reflected light can be led most efficiently to the time-analytical measuring apparatus 50.

Therefore, if the position is controlled by the controlling apparatus 52 so that the focal distance of the condensing lens 48 may be set in the observing position for the object of the examined body 2, the light reflected at any depth of the examined body 2 will be particularly more enhanced (than the light from another position) and will be able to be detected by the time-analytical measuring apparatus 50.

By the way, the angle $\theta$ where the reflected light can be detected is determined by the aperture rate of the condensing lens 48 and therefore the larger the aperture rate, the higher the detection sensitivity of the time-analytical measuring apparatus 50 as a result.

The controlling apparatus 52 controls the detection timing of the time-analytical measuring apparatus 50 in conformity with the entering timing of the enhanced reflected light from the focal distance of the condensing lens 48 and the time-analytical measuring apparatus 50 detects only the reflected light from the object position. When this is carried out at the respective depths of the examined body 2, the signal processing apparatus 53 will display through the monitor 8 the internal information of the examined body 2 on the basis of the obtained signal.

Figure 9:
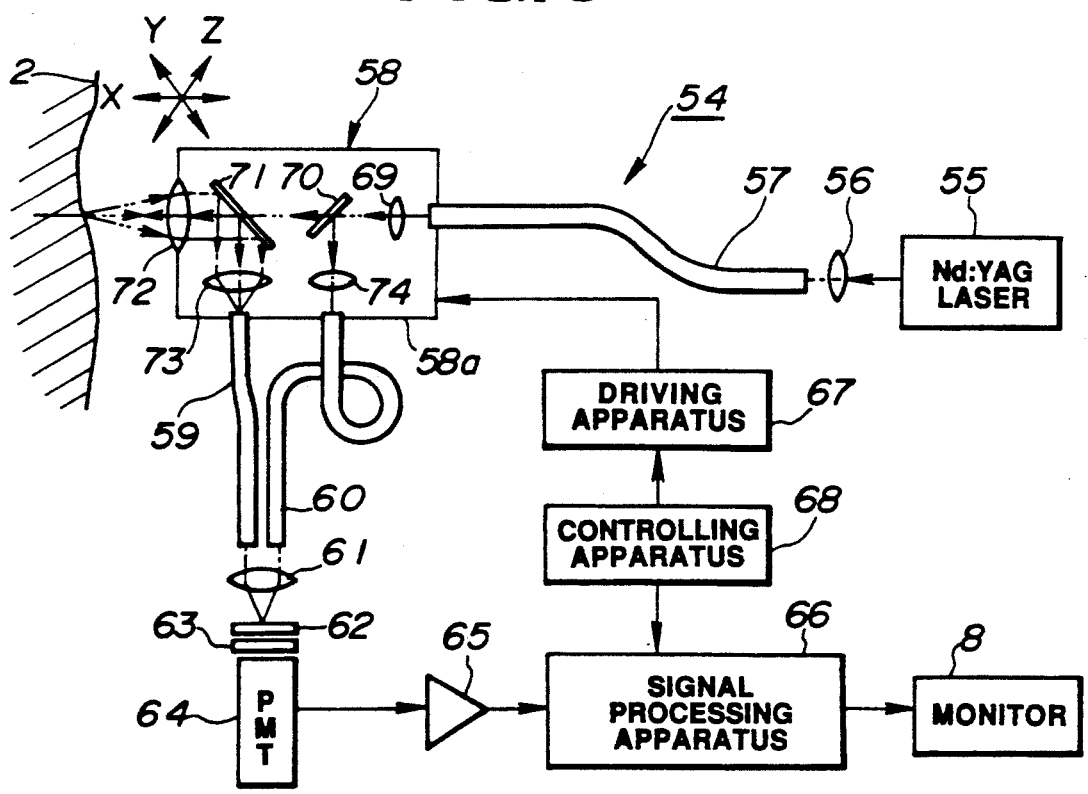

FIG. 9 shows an examined body interior information observing apparatus 54 as an example of this embodiment.

This examined body interior information observing apparatus 54 is provided with such light radiating means as an Nd:YAG laser 55 oscillating pulse laser lights, for example, of a picosecond unit, a lens 56 and first optical fiber bundle 57 leading the pulse laser lights from the Nd:YAG laser 55 and a scanning apparatus 58 for radiating to the examined body 2 as scanning lights the pulse laser lights from the emitting end of the first optical fiber bundle 57.

Also, the examined body interior information observing apparatus 54 is provided with a second optical fiber bundle 59 leading the reflected light from the examined body 2 coming through the above-mentioned scanning apparatus 58, a third optical fiber bundle 60 leading the reference light from the Nd:YAG laser 55 through the scanning apparatus 58, a lens 61 condensing the reflected light from the second optical fiber bundle 59 and the reference light from the third optical fiber bundle 60, a KDP as a non-linear optical crystal receiving the reflected light and reference light focused by the lens 61 and generating a second harmonic wave, an optical filter 63 passing only the second harmonic wave, a photo-multiplier tube (PMT) 64 detecting the second harmonic wave having passed through the optical filter 63 and a lock-in amplifier 65 amplifying the output signal of the photo-multiplier tube 64.

The time-analytical detecting means comprises the lens 61, KDP 62, optical filter 63, photo-multiplier tube (PMT) 64 and lock-in amplifier 65.

Further, the examined body interior information observing apparatus 54 comprises a computer or the like for analyzing and processing the output signal of the above-mentioned lock-in amplifier 65 and is provided with a signal processing apparatus 66 for the conversion to the cross-sectioned image and three-dimensional image of the examined body 2, a driving apparatus 67 as a variable means for three-dimensionally (X, Y and Z) moving the above-mentioned scanning apparatus 58 and a controlling apparatus 68 for controlling the position of the driving apparatus 67 and giving the position information of the scanning apparatus 58 to the above-mentioned signal processing apparatus 66. The monitor 8 receives the output signal of the signal processing apparatus 66 and displays the cross-sectioned image and three-dimensional image of the examined body 2.

The above-mentioned scanning apparatus 58 has a first lens 69, first beam splitter 70, second beam splitter 71 and condensing lens 72 leading the photo-pulse laser light from the emitting end of the first optical fiber bundle 57 to the examined body 2 and is provided with a second lens 73 leading to the entering end of the above-mentioned second optical fiber bundle 59 through the second beam splitter 71 the reflected light from the examined body 2 made parallel by the condensing lens 72, a third lens 74 leading to the entering end of the above-mentioned third optical fiber bundle 60 the reference light split by the first beam splitter 70 from the pulse laser light from the above-mentioned Nd:YAG laser 55 and an XYZ stage 58a driven by the above-mentioned driving apparatus 67 to make such optical system as the above-mentioned condensing lens 72 movable in X, Y and Z directions in FIG. 9.

Of the various lights split by the above-mentioned beam splitter 70, the light path length for the reflected light reflected in the focal distance of the condensing lens 72 to the above-mentioned lens 61 and the light path length for the reference light from the beam splitter 70 to the lens 61 are always adjusted to be equal to each other.

In this formation, the pulse laser light of a picosecond unit emitted from the Nd:YAG laser 55 is radiated to the examined body 2 through the lens 56, first optical fiber bundle 57, first beam splitter 70, second beam splitter 71 and condensing lens 72. The reflected light reflected by the examined body 2 enters the lens 61 through the condensing lens 72 again and through the second beam splitter 71, second lens 73 and second optical fiber bundle 59. The entering reflected light is the enhanced reflected light from the focal distance of the condensing lens 72.

The reference light split by the first beam splitter 70 enters the above-mentioned lens 61 through the third lens 74 and third optical fiber bundle 60.

The reflected light and reference light pass through the KDP 62 and photo-filter 63. The reflected light from the examined body 2 is detected time-analytically by the photo-multiplier tube 64 by the same operating principle as in the above-described apparatus in FIG. 4 and the output signal of the photo-multiplier tube 64 is amplified by the lock-in amplifier 65 and is output to the signal processing apparatus 66.

The driving apparatus 67 moves the XYZ stage 58a in the X direction (depth direction of the examined body 2) to make variable the focal distance of the condensing lens 72 and moves the XYZ stage 58a in the Y and Z directions to scan the pulse laser light from the condensing lens 72. Therefore, the signal processing apparatus 66 analyzes and processes the signals detected successively by the photo-multiplier tube 64 and processes the information within the examined body 2 to be a cross-sectioned image or three-dimensional image which is displayed by the monitor 8.

In this embodiment, the driving apparatus 67 operates so that the focal distance of the condensing lens 72 may be set in the observing position for the object of the examined body 2, the light reflected at any depth of the examined body 2 may be particularly better (than the light from another position) led and enhanced in proportion to the aperture rate of the condensing lens 72, therefore the information at the object depth may be efficiently detected by the photo-multiplier tube 64, the pulse laser light may be radiated as a scanning light to the examined body and therefore the information within the examined body 2 may be displayed as a cross-sectioned image and three-dimensional image.

Figure 10:
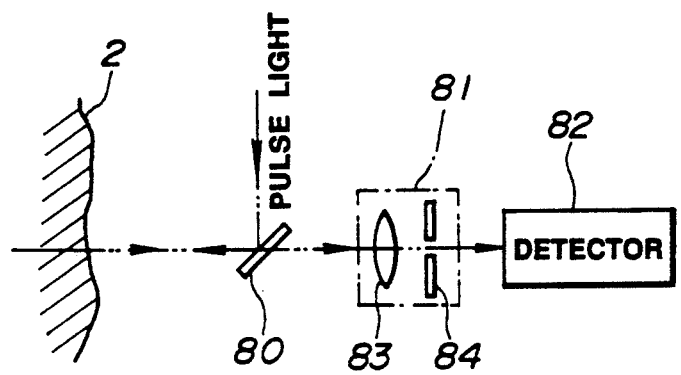

Now, in case the light is radiated to such examined body as a living body tissue, a part of the light will be dispersed by the tissue cells or the like and therefore the space resolution of the light detected by such dispersed light component will be deteriorated. Therefore, a detecting method by spatially suppressing the incident light by a collimator is considered as a means for properly suppressing the dispersion of a light. FIG. 10 shows an apparatus using a method of spatially suppressing the incident light.

This apparatus comprises a beam splitter 80 reflecting a pulse light from a photo-pulse generating apparatus, a collimator 81 suppressing only the dispersed component of the reflected light of the pulse light radiated to the examined body 2 through the beam splitter 80, reflected by the examined body 2 and passed again through the beam splitter 80 and a detector 82 detecting the reflected light from the examined body 2. The above-mentioned collimator 81 is formed of a lens 83 (of a magnification, for example, of 10 times) condensing the reflected light from the examined body 2 and a pinhole 84 (of a hole diameter, for example, of 10 times) condensing the reflected light from the examined body 2 and a pinhole 84 (of a hole diameter, for example of about 50 μm varying with the magnification of the lens) suppressing the dispersed component of the reflected light condensed by the lens 83.

In this formation, the dispersed component light of the reflected light from the examined body 2 is not a light substantially parallel with the optical axis and is therefore suppressed by the pinhole 84 and only the straight proceeding light component from the examined body 2 passes through the pinhole 84. The detector 8 can detect only the straight proceeding light component.

Figure 11:
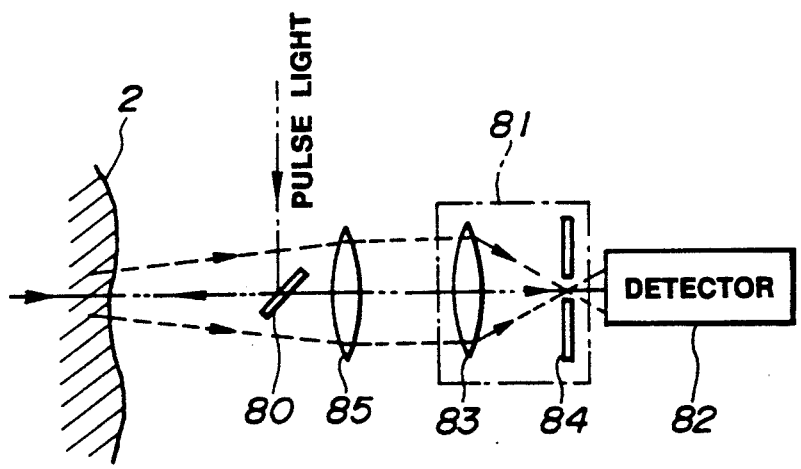

In FIG. 11, a condensing lens 85 is further provided in the apparatus of FIG. 10, the reflection angle of the reflected light from the examined body 2 is considered and the reflected light not parallel with the optical axis of the beam splitter 80 and pinhole 84 can also be detected.

The light which is not parallel with the above mentioned optical axis shown by the dotted line in FIG. 11 but is a reflected light from the focal distance of a lens 85 is made a parallel light by this lens 85 arranged between the above-mentioned beam splitter 80 and lens 83, passes through the pinhole 84 through the lens 83 and can be detected by the detector 82. The reflected light beams from the other positions are suppressed by the pinhole 84 and cannot be detected.

If the apparatus in FIGS. 10 or 11 is arranged in front of the above-mentioned time-analytical measuring apparatus in the first to third embodiments and modifications, the spatially dispersed component will be able to be suppressed and the internal information of the examined body 2 will be able to be detected with a higher resolution.

By combining the first embodiment, modification or second embodiment and third embodiment, for example, if the reflected light from the focal distance of a focus lens is detected by making variable the detection sensitivity of the time-analytical measuring apparatus, internal information of a higher sensitivity will be able to be detected.

Though a living body has been taken up for the examined body, the present invention can be applied also to examined objects other than a living body.

As described above, according to the first to third embodiments, in case the light radiated by the light radiating means becomes a reflected light within the examined body and this reflected light is detected by the time-analytical detecting means, by using at least one of the variable sensitivity means for making variable the detection sensitivity of the time-analytical detecting means in response to the depth of the examined body and the variable positioning means for making variable the position of the lens system sos that the reflected light from the observed position of the examined body may be used to indicate the depth of the examined body, the reflected light from the examined body will be time-analytically detected by the time-analytical detecting means and therefore the examined body interior information in the observed position for the object of the examined body can be more efficiently detected with high precision and high S/N without being influenced by the light intensity varying due to the depth of the examined body.

The fourth and fifth embodiments of the present invention describe an optical cross-sectioned image observing apparatus whereby a cross-sectioned image of a living body can be obtained without direct contact and non-invasively and which can be used together with the process shall be explained in the following.

The fourth embodiment is an example of combining an operating microscope and an optical cross-sectioned image observing apparatus.

Figure 12:
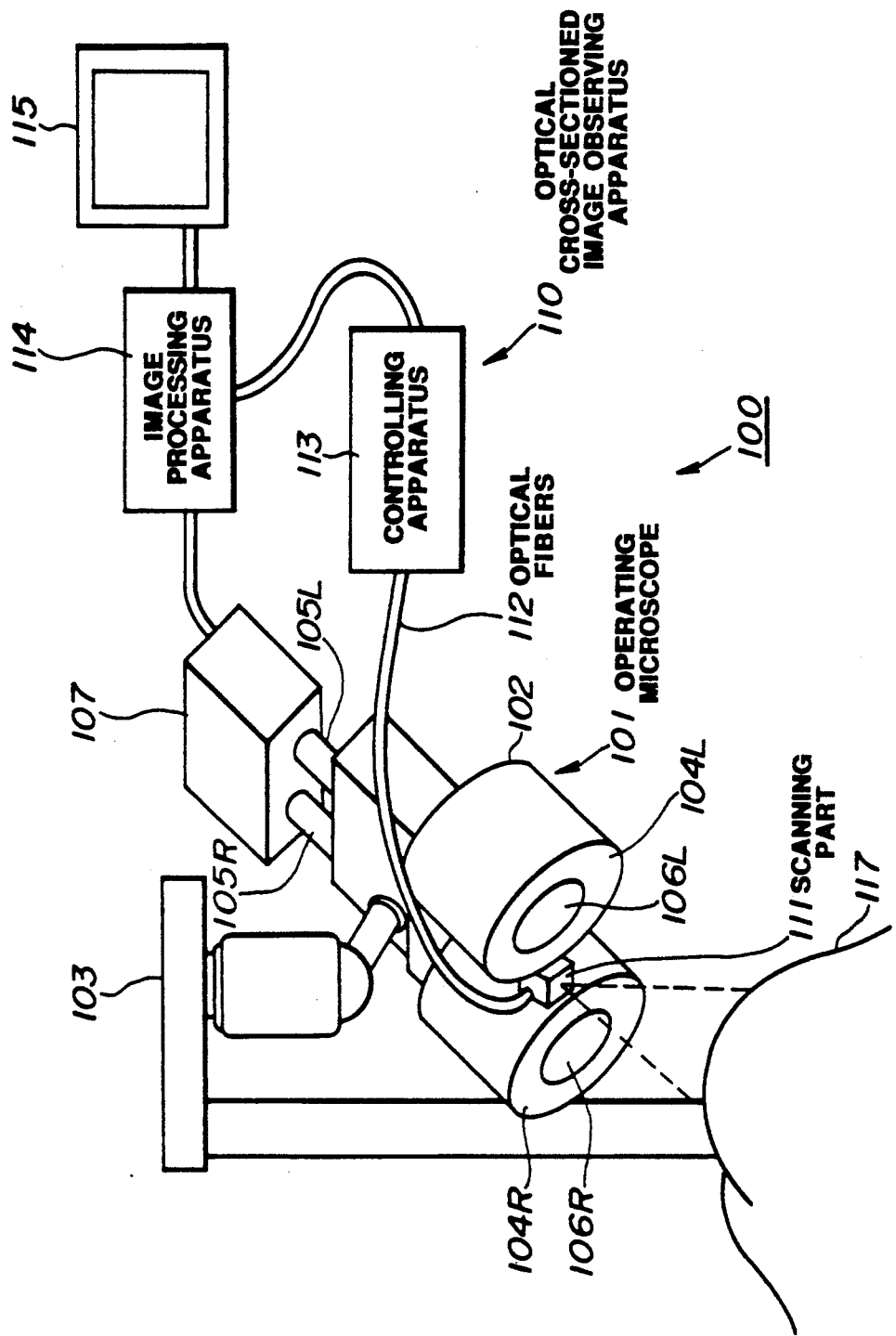

As shown in FIG. 12, an operating observing system 100 is provided with an operating microscope 101 and an optical cross-sectioned image observing apparatus 110 combined with this operating microscope 101. The above-mentioned operating microscope 101 comprises a microscope body 102 and an arm 103 movably supporting this microscope body 102. The above-mentioned microscope body 102 is of a binocular type and is provided with two objective parts 104R and 104L, two eyepiece parts 105R and 105L corresponding to the respective objective parts 104R and 104L and an illuminating apparatus not illustrated. The objective parts 104R and 104L are provided respectively with objective lenses 106R and 106L. The eyepiece parts 105R and 105L are provided respectively with eyepiece lenses not illustrated. A television camera 107 is removably connected to the above-mentioned eyepiece parts 105R and 105L.

On the other hand, an optical cross-sectioned image observing apparatus 110 comprises a scanning part 111 provided between the objective parts 104R and 104L of the above-mentioned microscope body 102, a controlling apparatus 113 connected through an optical fiber bundle 112 to this scanning part 111, an image processing apparatus 114 connected to this controlling apparatus 113 and a monitor 115 connected to this image processing apparatus 114. A video signal from the above-mentioned television camera 107 is also input into the above-mentioned image processing apparatus 114.

Figure 13:
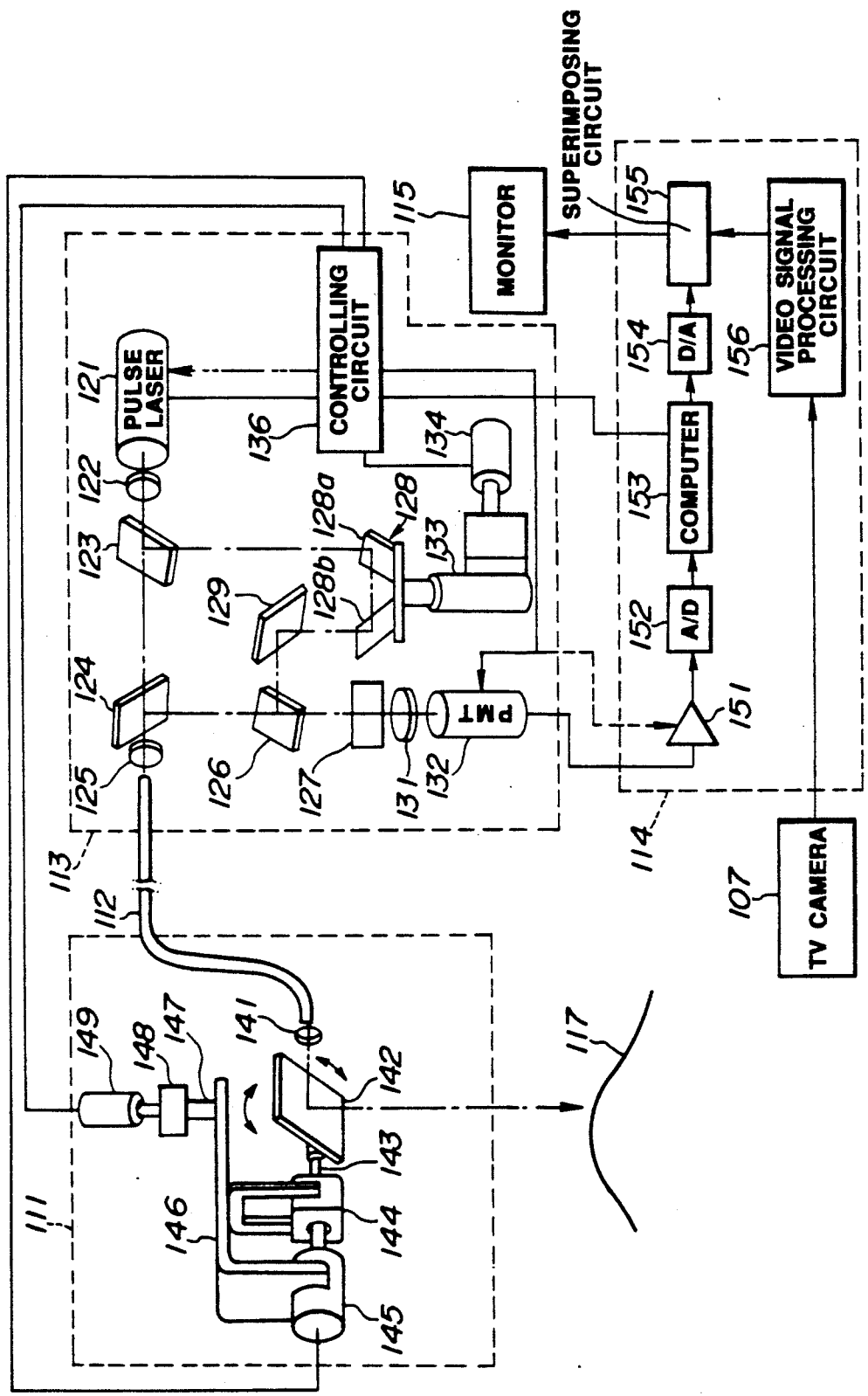

As shown in FIG. 13, the above-mentioned controlling apparatus 113 is provided with a pulse laser 121 emitting a pulse laser light for observing a cross-sectioned image so that the light emitted from this pulse laser 121 may pass through a lens 122 and beam splitters 123 and 124, may be condensed by a lens 125 and may enter the base end surface of the optical fiber bundle 112. This light is led to the scanning part 111 through the above-mentioned optical fiber bundle 112 and is radiated to the living body tissue 117 which is an object position to be treated from this scanning part 111.

The returning light reflected within this living body tissue 117 is led to the above-mentioned controlling apparatus 113 by the above-mentioned optical fiber bundle 112. This returning light is emitted from the base end of the optical fiber bundle 112, passes through the lens 125, is reflected by the beam splitter 124, passes through a half mirror 126 and enters a KDP 127 as a non-linear optical crystal. On the other hand, the pulse light emitted from the pulse laser 121 and reflected by the above-mentioned beam splitter 123 is reflected by a mirror 129 through a delaying mirror part 128 having two mirrors 128a and 128b, is reflected by the above-mentioned half mirror 126 and enters the above-mentioned KDP 127 as a reference light. The above-mentioned KDP 127 generates a second harmonic wave by inputting the returning light from the living body tissue and the above-mentioned reference light.

This second harmonic wave passes through a filter 131 which passes only this second harmonic wave and is detected by a photo-multiplier tube 132. Also, the above-mentioned delaying mirror part 128 is moved by a moving apparatus 133 driven by a motor 134 to vary the light path length of the above-mentioned reference light. The intensity of the second harmonic wave generated by the above-mentioned KDP 127 is proportional to the integrated value of the product of the returning light and reference light in case the above-mentioned returning light and reference light are respectively made functions of time. Therefore, by varying the light path length of the reference light by driving the above-mentioned delaying mirror part 128, the intensity of any time component of the returning light from the interior of the living body tissue 117 can be detected by the photo-multiplier tube 132. Thus, the time analysis waveform of the returning light from the interior of the living body tissue 117 can be detected. A controlling circuit 136 controlling the above-mentioned pulse laser 121 and motor 134 is provided within the controlling apparatus 113.

The above-mentioned scanning part 111 is provided with a lens 141 and scanning mirror 142 opposed to the tip surface of the above-mentioned optical fiber bundle 112 and arranged on the optical axis of the optical fiber bundle 112. The above-mentioned scanning mirror 142 is fixed to a rotary shaft 143 which is connected to the output shaft of a motor 145 through a gear box 144. The above-mentioned gear box 144 and motor 145 are supported by a supporting member 146 which is fixed to a rotary shaft 147 arranged so as to intersect at right angles with the above-mentioned rotary shaft 143. This rotary shaft 147 is connected to the output shaft of a motor 149 through a gear box 148. In such formation, by rotating the motors 145 and 149, the scanning mirror 142 can be rotated and driven in two directions so that the position of the light reflected by the scanning mirror 142 and radiated to the living body tissue 117 may be two-dimensionally scanned.

The above-mentioned motors 145 and 149 are controlled by the controlling circuit 136 within the controlling apparatus 113. This controlling circuit 136 controls the detection sensitivity of the photo-multiplier tube 132 or the gain of the lock-in amplifier 151 in response to the variation of the light path length of the above-mentioned reference light.

In case the reflected light in the part near the surface is to be detected by making this light path length small, the detection sensitivity or gain will be reduced and, in case the reflected light from the deep part is to be detected by making the light path length large, the detection sensitivity or gain will be controlled to be elevated.

The above-mentioned image processing apparatus 114 comprises the lock-in amplifier 151 amplifying the output signal of the above-mentioned photo-multiplier tube 132, an A/D converter 152 A/D-converting the output signal of this lock-in amplifier 151, a computer 153 inputting the output signal of this A/D converter 152, a D/A converter 154 D/A-converting the output signal of this computer 153, a video signal processing circuit 156 processing the output signal of the above-mentioned television camera 107 to be a video signal and a superimposing circuit 155 synthesizing the output signal of the above-mentioned D/A converter 154 and the output signal of the above-mentioned video signal processing circuit 156. The output signal of the above-mentioned superimposing circuit 155 is input into the monitor 115. The information of the scanning position from the controlling circuit 136 within the controlling apparatus 113 is input into the above-mentioned computer 153.

The operation of this embodiment shall be explained in the following with reference to FIGS. 14 and 15.

The operation by utilizing the operating observation system of this embodiment is made while observing the optical image of the living body tissue 117 in the treatment object position with the operating microscope 101. In this operation, particularly in case the information within the living body tissue 117 is wanted to be known, the optical cross-section image observing apparatus 110 will be used. Such pulse light as is shown in FIG. 15a is emitted from the pulse laser 121 within the controlling apparatus 113 and enters the optical fiber bundle 112 through the lens 122, beam splitters 123, 124 and lens 125.

This pulse light is led to the scanning part 111 by the optical fiber bundle 112, passes through the lens 141, is reflected by the scanning mirror 142 and is radiated to the living body tissue 117. This light is partly reflected by the boundary surfaces different in the refractive index within the living body tissue 117 and such returning light as is shown in FIG. 15b enters the above-mentioned scanning part 111. This returning light is reflected by the scanning mirror 142, passes through the lens 141, enters the optical fiber bundle 112 and is led to the controlling apparatus 113 by this optical fiber bundle 112. This returning light enters the KDP 127 through the lens 125, beam splitter 124 and half mirror 126.

Also, the pulse light emitted from the pulse laser 121 and reflected by the beam splitter 123 enters the above-mentioned KDP 127 through the delaying mirror part 128, mirror 129 and half mirror 126. The second harmonic wave generated by the above-mentioned KDP 127 passes through the filter 131 and is detected by the photo-multiplier tube 132. At this time, when the above-mentioned delaying mirror part 128 is moved to vary the light path length of the reference light, the intensity of any time component of the above-mentioned returning light will be able to be detected. If the reference lights of such timings as, for example, in FIGS. 15c and 15e are used, as shown respectively in FIGS. 15d and 15f, the second harmonic waves of the intensities corresponding to the time components of the returning lights in the timings of the respective reference lights will be generated from the KDP 127. The output signal of the above-mentioned photo-multiplier tube 132 is taken into the computer 153 through the amplifier 151 and A/D converter 152 and the time-analyzed waveform of the returning light, that is, the intensity distribution of the returning light against the depth of the living body tissue 117 can be determined.

The above operation is repeated by moving the scanning mirror 142 within the scanning part 111 and two-dimensionally scanning the living body tissue 117 and the intensity distribution of the returning light in each position is determined. By the computer 153, by using the intensity distribution of the returning light in each position, the optical cross-sectioned image within the living body tissue 117 is formed and is output as a digital video signal. This video signal is input into the superimposing circuit 155 through the D/A converter 154.

Also, the optical image of the surface of the living body tissue 117 is photographed by the television camera 107 fitted to the eyepiece parts 105R and 105L of an operation microscope 101. The output signal of this television camera 107 is processed by the video signal processing circuit 156 and the video signal of the above-mentioned optical image is output from this video signal processing circuit 156.

The video signal of the cross-sectioned image from the above-mentioned D/A converter 154 and the video signal of the optical image from the video signal processing circuit 156 are synthesized by the above-mentioned superimposing circuit 155 and are output to the monitor 115. Therefore, as shown, for example, in FIG. 14, the optical image 161 of the surface of the living body tissue 117 obtained by the operating microscope 101 and the cross-sectioned image 162 within the living body tissue 117 are displayed in the monitor 115. As shown in FIG. 14, an optical cross-section concerning region 163 which is a scanning range for obtaining the above-mentioned cross-sectioned image 162 may be displayed on the above-mentioned optical image 161. In FIG. 14, the cross-sectioned image is displayed three-dimensionally but may be displayed two-dimensionally.

According to this embodiment, a cross-sectioned image of a living body can be obtained without direct contact and non-invasively and can be used together with the treatment.

Instead of controlling the detection sensitivity of the photo-multiplier tube 132 or the gain of the lock-in amplifier 151 by the controlling circuit 136 in response to the variation of the light path length of the above-mentioned reference light, the light emitting power of the photo-pulse emitted from the pulse laser 121 may be controlled. The control signal for making this control is shown by the two-point chain line in FIG. 13.

The fifth embodiment of the present invention shall be explained in the following with reference to FIGS. 16 and 17.

This embodiment is an example of combining a rubber scope which is a rigid endoscope for observing and treating an abdomen interior and an optical cross-sectioned image observing apparatus.

Figure 16:
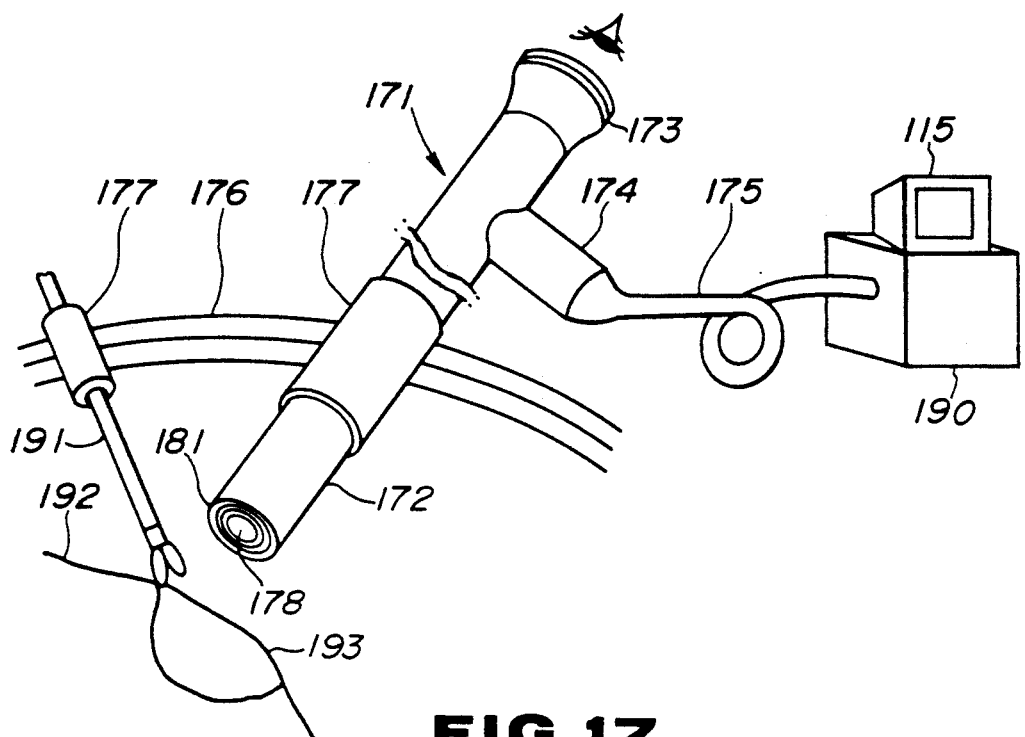
FIGS. 16 and 17 relate to the fifth embodiment of the present invention.

As shown in FIG. 16, the operating observing system comprises a rubber scope 171, an optical cross-sectioning apparatus 190 connected to this rubber scope 171 and a monitor 115 connected to this optical cross-sectioning apparatus 190.

The above-mentioned rubber scope 171 comprises a rigid elongate insertable section 172, an eyepiece section 173 provided at the rear end of this insertable section 172, a buckling preventing section 174 provided on the side of the rear end side of the above-mentioned insertable section 172 and a cable section 175 extended from this buckling preventing section 174 and connected at the end to the optical cross-sectioning apparatus 190. The above-mentioned insertable section 172 is to be led on the tip side into a body cavity through a tragacanth sheath driven into a body cavity wall 176.

Figure 17:
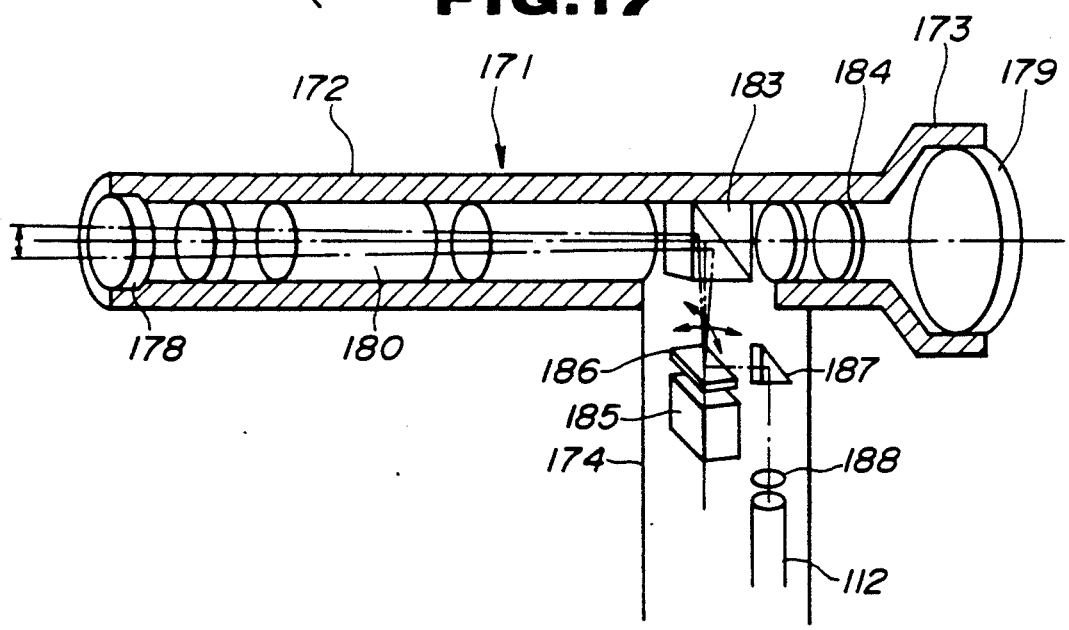

As shown in FIG. 17, an objective lens 178 is provided within the tip part of said insertable section 172, an eyepiece lens 179 is provided within the eyepiece section 173 and a relay lens system 180 transmitting an object image formed by the above-mentioned objective lens 178 to the eyepiece lens 179 is provided within the insertable section 172. Also, as shown in FIG. 16, a light guide 181 is provided on the outer peripheral side of the above-mentioned relay lens system 180 within the above-mentioned insertable section 172.

In FIG. 17, the above-mentioned light guide 181 is not illustrated. This light guide 181 is inserted on the base side through the buckling preventing section 174 and cable section 175 and is connected to the above-mentioned optical cross-sectioning apparatus 190 so that an illuminating light emitted from a light source apparatus, not illustrated, provided within this optical cross-sectioning apparatus 190 may be radiated to an observed position from the tip part of the insertable section 172 through the above-mentioned light guide 181. An optical image of the observed position illuminated by this illuminating light is formed by the objective lens 178, is transmitted to the eyepiece section 173 by the relay lens system 180 and is observed from this eyepiece section 173.

As shown in FIG. 17, in this embodiment, a beam splitter 183 is provided in the position corresponding to the buckling preventing section 174 within the relay lens system 180. A laser light wavelength region cutting filter 184 for observing the cross-sectioned image is provided between the rear end of the relay lens system 180 and the eyepiece lens 179. A galvanomirror 186 moved in two directions intersecting at right angles with each other by a driving apparatus 185, a reflecting prism 187, a lens 188 and one end part of the optical fiber bundle 112 are arranged on the same optical axis within the buckling preventing section 174.

The formation of the above-mentioned optical cross-sectioning apparatus 190 is substantially the same as of the combination of the controlling apparatus 113 and image processing apparatus 114 shown in FIG. 13 except having the above-described light source apparatus. However, in the optical cross-sectioning apparatus 190, the superimposing circuit 155 and video signal processing circuit 156 in the fourth embodiment do not exist and the output signal of the D/A converter 154 is input directly into the monitor 115. Also, the above-mentioned driving apparatus 185 is controlled by the controlling circuit 136.

The operation of this embodiment shall be explained in the following.

In the case of making an operation by utilizing the operating observing system of this embodiment, as shown in FIG. 16, the insertable section 172 of the rubber scope 171 is led into a body cavity through the tragacanth sheath 177 driven into the body cavity wall 176 and an operating treating instrument 191 is also led into the body cavity through another tragacanth sheath 177. Under an ordinary observation from the eyepiece section 173 of the rubber scope 171, the affected part 193, for example, of an organ 192 is treated by using the treating instrument 191.

In the case of this operation, particularly in case the information within the affected part 193 is wanted to be known, the same as in the fourth embodiment, a pulse light is emitted from the pulse laser 121 into the optical cross-sectioning apparatus 190. This pulse light passes through the optical fiber bundle 112 and lens 188, is reflected by the reflecting prism 187 and galvanomirror 186, is reflected by the beam splitter 183, passes through the relay lens system 180 and objected lens 178 and is radiated to the affected part 193. At this time, by driving the galvanomirror 186, the position of the pulse light radiated to the affected part 193 will be varied and the affected part 193 will be scanned.

The returning light reflected within the affected part passes through the objective lens 178 and relay lens system 180, is reflected by the beam splitter 183 and is led to the optical cross-sectioning apparatus 190 through the galvanomirror 186, reflecting prism 187, lens 188 and optical fiber bundle 112. The same process as in the fourth embodiment is made in this optical cross-sectioning apparatus 190 and an optical cross-sectioned image of the affected part 193 is displayed in the monitor 115.

For example, a near infrared laser light is used for this cross-sectioned image observing pulse light. In such case, the filter 184 provided in the rubber scope 171 shall be a near infrared ray cutting filter so that an ordinary optical image may be observed even at the time of observing the cross-sectioned image. Instead of the above-mentioned filter 184, a shutter may be provided so as to be closed at the time of observing the cross-sectioned image.

The other formations, operations and effects are the same as in the fourth embodiment.

The present invention is not limited to the above-mentioned fourth and fifth embodiments, for example, the light radiated to the object position of the examined body is not limited to the pulse light but may be a modulated light or the like.

Also, the optical cross-sectioned image may be observed by using a light having passed through the object position.

According to the above-mentioned fourth and fifth embodiments, because the means for obtaining the optical image of the object position of the examined body and the means for obtaining the optical cross-sectioned image of the above-mentioned object position are provided, there is an effect that, in the case of treating a living body, a cross-sectioned image of the object position of the treatment will be able to be obtained without direct contact and non-invasively.

A cross-sectioned image observing light scanning apparatus whereby the light necessary for observing a cross-sectioned image can be positively scanned with a simple operation shall be explained below.

The cross-sectioned image observing light scanning apparatus of the sixth embodiment of the present invention is provided in the insertable section to be inserted into an examined body with a means for scanning the light for observing a cross-sectioned image radially from the above-mentioned insertable section so that the light scanning may be made easy.

Figure 18:
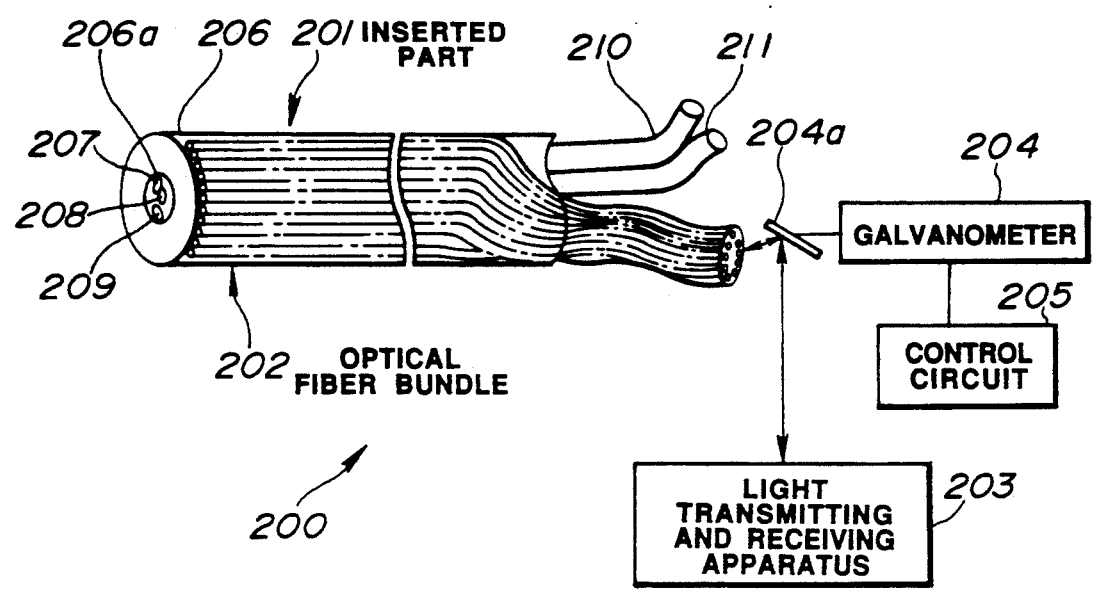
FIGS. 18 to 20 show the sixth embodiment of the present invention.

As shown in FIG. 18, a cross-sectioned image observing light scanning apparatus 200 comprises an elongate flexible insertable section 201 to be inserted into an examined body, a light transmitting and receiving apparatus 203 for emitting photo-pulses for observing a cross-sectioned image and receiving a reflected light from the interior of the examined body, a galvanometer 204 and a controlling circuit 205 controlling this galvanometer 204.

The above-mentioned insertable section 201 is formed as an insertable section, for example, of an endoscope and has an illuminating window 207, observing window 208 and sucking channel 209 formed in a channel part 206a of a tip part 206.

A light distributing lens, not illustrated, is fitted inside the above-mentioned illuminating window 207 and a light guide 210 is connected to the rear end of this light distributing lens, is then inserted through the above-mentioned insertable section 201, is then connected to a light source apparatus, not illustrated, transmits an illuminating light from this light source apparatus and then radiates it to the observed position of the examined body from the above-mentioned illuminating window 207.

Also, an objective lens, not illustrated, is provided inside the above-mentioned observing window 208 and the tip surface of an image guide 211 is arranged in the image forming position of this objective lens. This image guide 211 is inserted through the above-mentioned insertable section 201 and is opposed on the rear end surface to an eyepiece lens within an eyepiece section not illustrated so that the optical image of the observed position formed by the above-mentioned objective lens may be led by the above-mentioned image guide 211 and may be observed with a naked eye from the above-mentioned eyepiece part.

Figure 19:
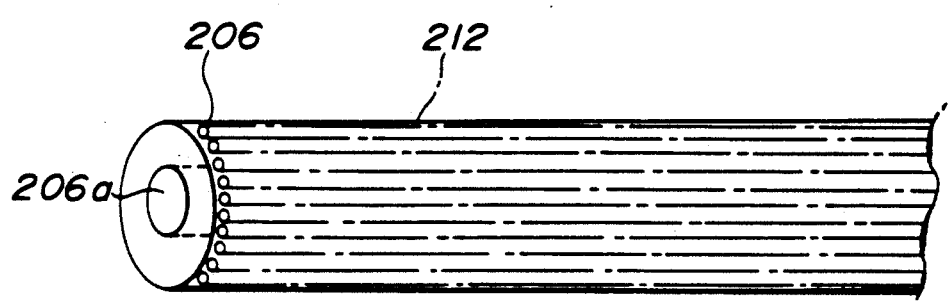
Figure 20:
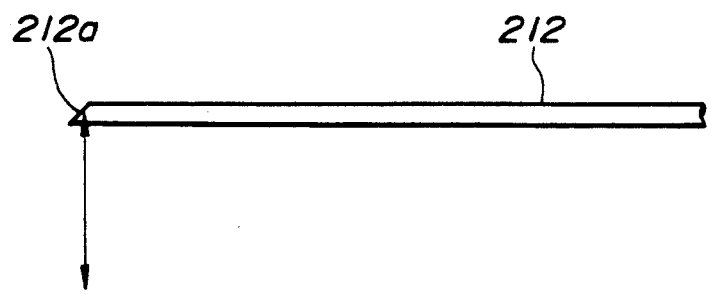

Also, an optical fiber bundle 202 used as a means for radially scanning the light for observing the cross-sectioned image is provided in the above-mentioned insertable section 201 and is formed of a plurality of optical fibers 212 annularly (cylindrically) arranged on the outer peripheral side of the above-mentioned insertable section 201. As shown in FIG. 19, the tips of the above-mentioned optical fibers 212 are arranged so as to enclose the above-mentioned channel section 206a on the outer peripheral side of the above-mentioned tip part 206 and, as shown in FIG. 20, the fiber is cut at the tip, for example, at 45 degrees with the fiber axis to form a tapered surface 212a.

Then, aluminum, silver or gold is evaporatively deposited on this tapered surface 212a to form a mirror surface. Such mirror surfaces are arranged to be inside at the tip of the above-mentioned insertable section 201 so that the light from the above-mentioned light transmitting and receiving apparatus 203 may be radiated sidewise (in the radial direction of the cylinder) of the fiber axis and the reflected light reflected from the interior of the examined body may be led in the fiber axial direction.

The above-mentioned light transmitting and receiving apparatus 203 is provided within with a pulse laser emitting photo-pulses, for example, of a picosecond unit, a lens and mirror group for forming a light path of the photo-pulses emitted from this pulse laser and an imaging means.

When a photo-pulse is emitted from the pulse laser of the above-mentioned light transmitting and receiving apparatus 203, the swing angle of the mirror 204a of the above-mentioned galvanometer 204 will be controlled by the above-mentioned controlling circuit 205 as operatively connected with the emission of this photo-pulse and the photo-pulse will enter the respective optical fibers 212 of the above-mentioned optical fiber bundle 202.

Figure 21:
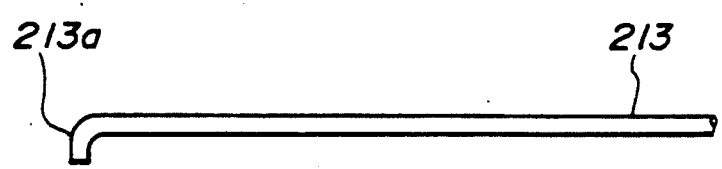

The above-mentioned optical fiber 212 may have a prism arranged without forming the tapered surface 212 at the end or, instead of the above-mentioned optical fiber 212, an optical fiber 213 bent at the tip part 213a in the outside direction from the above mentioned insertable section 201, as shown in FIG. 21, may be used to form the above-mentioned optical fiber bundle 202.

An optical cross-sectioned image observation by using the above-mentioned cross-sectioned image observing light scanning apparatus shall be explained below.

In the case of observing an optical cross-sectioned image, for example, of the affected part of an organ of a human body, first of all, the insertable section 201 will be inserted into the body cavity. Then, when the outer peripheral side of the tip part 206 reaches the affected part position, a photo-pulse of a very short time width of a half value width of several picoseconds will be generated from the pulse laser within the light transmitting and receiving apparatus 203. This photo-pulse is reflected by the mirror 204 of the galvanometer 204 and enters the respective optical fibers 212 forming the optical fiber bundle 202.

The photo-pulse having entered each above-mentioned optical fiber 212 is reflected by the tapered surface 212a at the tip, is radiated sidewise from the fiber axis and is photo-scanned radially outward from the above-mentioned optical fiber bundle 202. When the light radiated to the affected part is reflected by the tissue surface and interior, this reflected light will be led into the above-mentioned light transmitting and receiving apparatus 23 through the mirror 204 of the above-mentioned galvanometer 204 from the above-mentioned optical fiber bundle 202 and will enter such imaging means as, for example, a streak camera through the internal lens and mirror group.

The time-analyzed waveform of the above-mentioned reflected light is detected in the above-mentioned streak camera and is processed by a processing apparatus, not illustrated, to obtain a cross-sectioned image of the observed position which is displayed in a displaying apparatus, also not illustrated. The detection sensitivity of this streak camera is controlled the same as in the above-described embodiment.

According to this embodiment, in case the above-mentioned insertable section 201 is inserted into the examined body interior and the cross-sectioned image is observed, without requiring a complicated operation of curving the above-mentioned insertable section 201, by only inserting the outer peripheral side of the tip part 206 of the above-mentioned insertable section to the observed position, the photo-scanning will be radially made from the above-mentioned insertable section 201 and therefore the cross-sectioned image of the desired observed position will be easily obtained.

Figure 22:
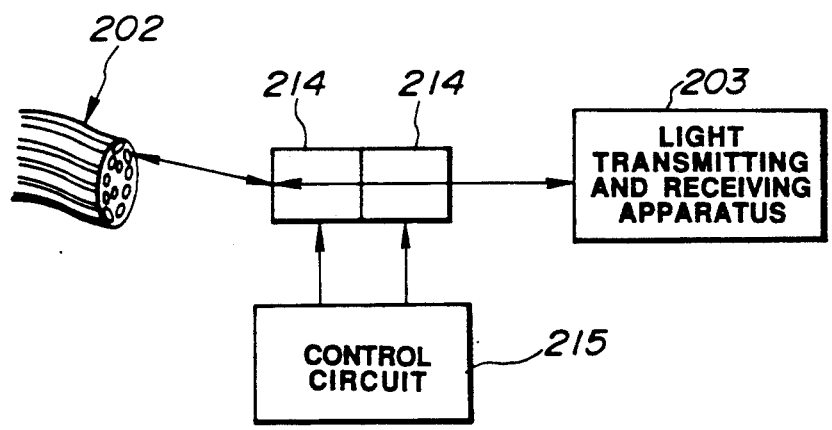
FIGS. 21 and 22 show a modification of the sixth embodiment.

Instead of the above-mentioned galvanometer 204, as shown in FIG. 22, and AOM (acoustic optical means) 214 may be arranged between the above-mentioned optical fiber bundle 202 and light transmitting and receiving apparatus 203 so that, by controlling this AOM 214 with the controlling circuit 215, the light from the above-mentioned light transmitting and receiving apparatus may be scanned and controlled.

According to this sixth embodiment, because the insertable section to be inserted into the examined body is provided with a means for radially scanning the light for the observation of the cross-sectioned image from the above-mentioned insertable section, the photo-scanning is made easy and the cross-sectioned image can be positively obtained.

An optical cross-sectioned image observing apparatus of the seventh embodiment which can be used as inserted into a vein shall be explained below.

Figure 23:
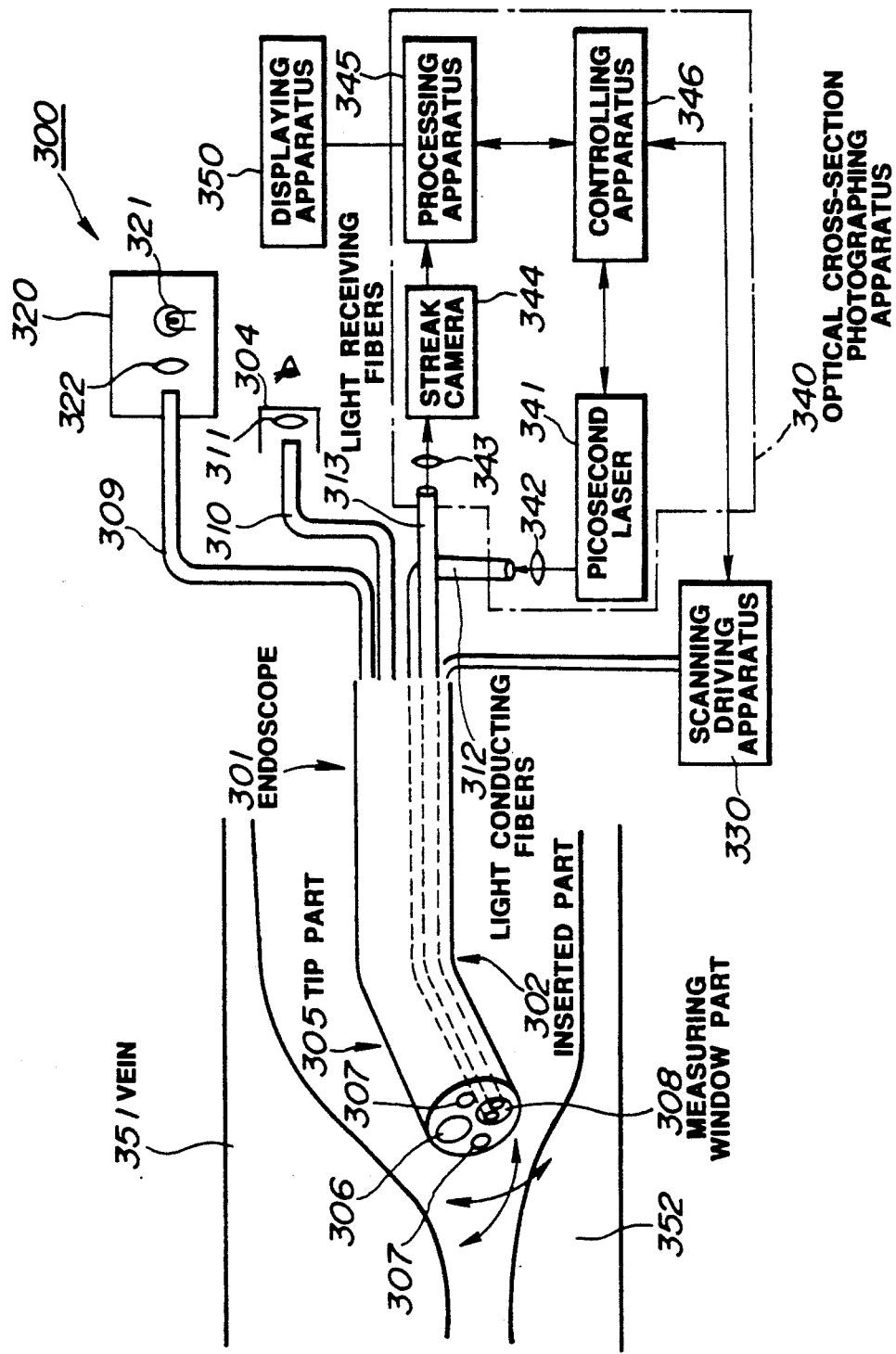
Figure 24:
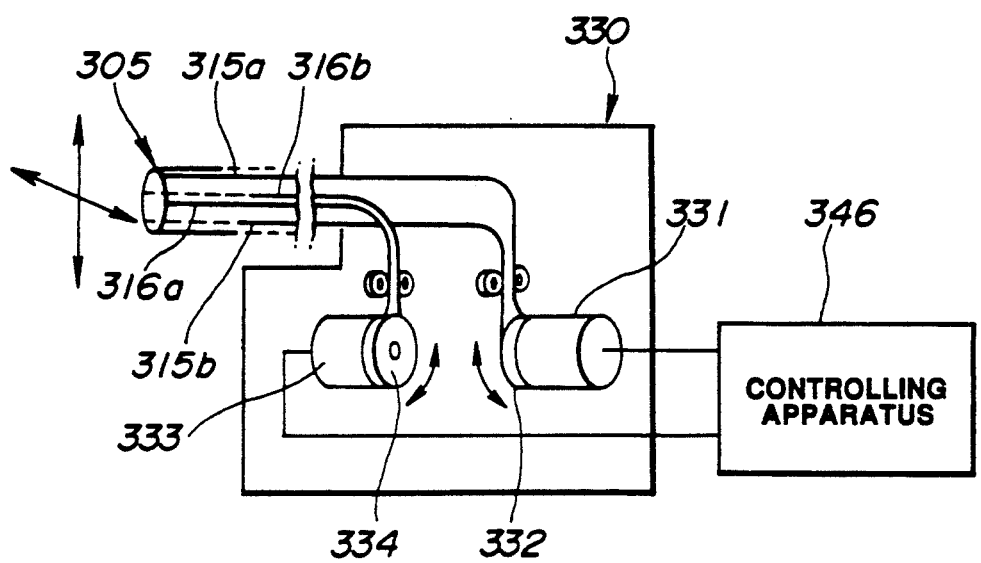

As shown in FIG. 23, an optical cross-sectioned vein endoscope apparatus 300 comprises an endoscope 301, a light source apparatus 320, scanning driving apparatus 330 and optical cross-section photographing apparatus 340 connected with this 10 endoscope 301 and a displaying apparatus 350 connected to the above-mentioned optical cross-section photographing apparatus 340.

The above-mentioned endoscope 301 comprises an elongate flexible insertable section 302 to be inserted into a vein 351, an operating section, not illustrated, provided on the base side of this insertable section 302 and an eyepiece section 304 provided at the rear end of this operating section. The above-mentioned insertable section 302 is provided in the tip part 305 with an observing window 306, illuminating window 307 and measuring window 308. A light distributing lens, not illustrated, is fitted inside the above-mentioned illuminating window and is connected at the rear end with a light guide 309 which is inserted through the insertable section 302 and is connected at the entrance end to the above-mentioned light source apparatus 320. This light source apparatus 320 is provided with a lamp 321 emitting an illuminating light and a condensing lens 322 condensing the emitted light of this lamp 321 to enter the above-mentioned light guide 309 at the entrance end. The emitted light of the above-mentioned lamp 321 is emitted from the illuminating window through the light guide 309 and light distributing lens and is radiated to the observed position.

An objective lens, not illustrated, is provided inside the above-mentioned observing window 307 and the tip surface of an image guide 310 is arranged in the image forming position of this objective lens. This image guide 310 is inserted through the insertable section 302 and is opposed at the rear end to an eyepiece lens 311 within the above-mentioned eyepiece section 304 so that the optical image of the observed position formed by the above-mentioned objective lens may be led to the eyepiece section 304 and may be observed from this eyepiece section 304.

Also, the respective tip surfaces of a light leading fiber bundle 312 and light receiving fiber bundle 313 as light transmitting means are arranged inside the above-mentioned measuring window part 308. Both fiber bundles 312 and 313 are inserted through the insertable section 302 and are connected at the rear ends to the above-mentioned optical cross-section photographing apparatus 304.

The above-mentioned tip part 305 has a curvable part consisting, for example, of a plurality of curved frames connected rotatably with each other so as to be curvable in both the vertical and horizontal directions.

Also, as shown in FIG. 4, four curving operating wires 315a, 315b, 316a and 316b are inserted through the above-mentioned insertable section 302. The vertically curving wires 315a and 315b are fixed at the tips to vertical positions within the tip part 305 of the insertable section 302 and the horizontally curving wires 316a and 316b are fixed at the tips to horizontal positions within the tip part 305 of the insertable section 302. The above-mentioned wires 315a, 315b, 316a and 316b are connected on the base sides to a scanning driving apparatus 330 provided with a vertically curving step motor 331 and horizontally curving step motor 333. Pulleys 332 and 334 are fitted, respectively, to the output shafts of the respective motors 331 and 333. The wires 315a and 315b are fitted to the pulley 332 and the wires 316a and 316b are fitted to the pulley 334 so that, when the motor 331 is rotated, the wires 315a and 315b will be pushed and pulled and the tip part 305 will be curved and driven in the vertical direction and, when the motor 333 is rotated, the wires 316a and 316b will be pushed and pulled and the tip part 305 will be curved and driven in the horizontal direction.

The above-mentioned optical cross-section photographing apparatus 340 comprises a picosecond laser 341 emitting a laser pulse light of a picosecond unit, a lens system 342 condensing the emitted laser light of this laser 341 to enter the above-mentioned light leading fiber bundle 312, a lens system 343 condensing the light led by the above-mentioned light receiving fiber bundle 313, a streak camera 344 receiving the light condensed by this lens system 343, a processing apparatus 345 processing the output signal of this streak camera 344 and a controlling apparatus 346 controlling the above-mentioned laser 341, processing apparatus 345 and scanning driving apparatus 330. The output signal of the above-mentioned processing apparatus 345 is input into a displaying apparatus 350. The wavelength of the emitted light of the above-mentioned picosecond laser 341 is, for example, 600 to 1200 nm high in the tissue transmittivity.

The operation of this embodiment shall be explained below.

Figure 25A:
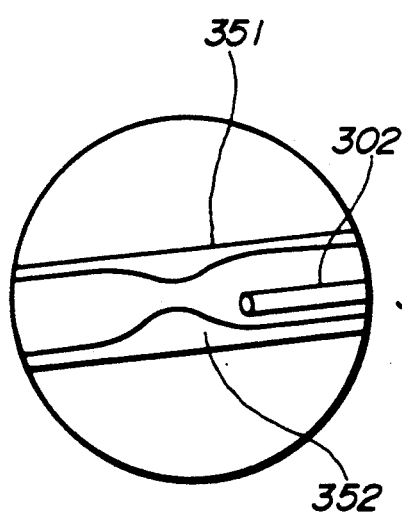
Figure 25:
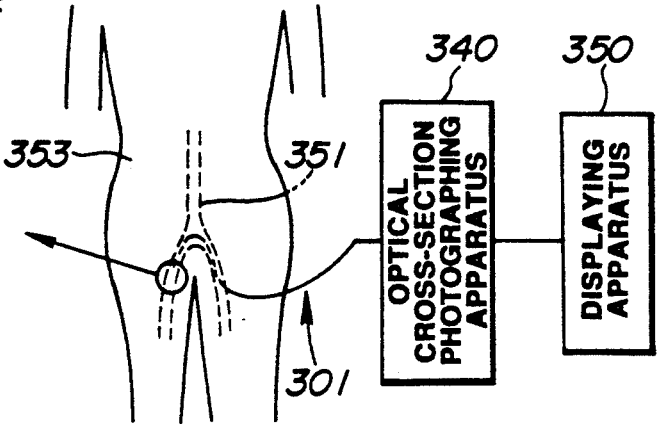

When observing an optical cross-sectioned image of a vein, first of all, as shown in FIG. 25, the insertable section 302 of the endoscope 301 will be inserted into a vein 351 of a human body 353. When the tip part 305 reaches such affected part as, for example, an atheroma, such extremely ultrashort pulse light of a half value width of several picoseconds, as is shown in FIG. 27a, will be generated from a picosecond laser 341 within the optical cross-section photographing apparatus 340 and will enter the light leading fiber bundle 312 through the lens system 342. This light is radiated to the measured position from the measuring window part 308 through the light leading fiber bundle 312 and is partly reflected by the boundary surfaces different in the refractive index within the measured position. This reflected light enters the tip surface of the light receiving fiber bundle 313 within the measuring window part 308, is led to the optical cross-section photographing apparatus 340 through this light receiving fiber bundle 313, passes through the lens system 343 and enters the streak camera 344. This streak camera 344 detects the time-analyzed waveform of the above-mentioned reflected light and transmits it to the processing apparatus 345. The above-mentioned time-analyzed waveform is shown in FIG. 27b in which the time corresponds to the depth from the measured position surface.

As operatively connected with the emission of the pulse light of the picosecond laser 341 by the control of the controlling apparatus 346, the tip part 5 is driven in the vertical and horizontal directions by the scanning and driving apparatus 330, the measured position is surface-like scanned, the above-mentioned operation is repeated, the time-analyzed waveform is detected in each position and the information necessary for the three-dimensional display of the measured position interior is accumulated in the processing apparatus 345. The processing apparatus 345 forms the cross-sectioned image or three-dimensional image of the measured position interior on the basis of this information.

When, as shown in FIG. 26, the angle $\psi$ of one direction of two directions intersecting at right angles with each other is made constant and the tip part 305 is scanned in the other direction (angle $\Theta$ direction), as shown in FIG. 27b, the time-analyzed analyzed waveform of the reflected light in each angle will be detected. When this time-analyzed waveform is processed by the processing apparatus 345, such cross-sectioned image of the measured position interior as is shown in FIG. 27c will be obtained. Further, when the tip part 305 is scanned also in the angle $\psi$ direction, such three-dimensional image of the measured position interior as is shown in FIG. 27d will be obtained. The display in the display apparatus 350 may be such two-dimensional or three-dimensional display, as is shown in FIG. 27c or 27d, or may be only a one-dimensional (depth direction) display.

Thus, according to this embodiment, the formation of the vein wall interior and the progress of the disease can be displayed in images so that an accurate diagnosis of such affected part as by the atheroma and the monitoring in such therapy as the intravein forming technique of the affected part may be possible.

Also, when such light source in which the wavelength can be varied as the dye laser is utilized, the wavelength of the light radiated to the measured position is varied, the reflected light from the measured position in a plurality of wavelengths is detected and the operation is made between the detected signals, not only the internal structure but also the biochemical information (for example, the coalized degree and the oxygenized state of hemoglobin or myoglobin) will be able to be diagnosed.

In the observation by the conventional vein endoscope, it is necessary to inject a physiological saline solution to secure the visual field at the time of the observation but, in this embodiment, as the time-analyzed waveform of the reflected light is detected, only the reflected light within the measured position can be extracted, the influence of the light dispersion by blood can be suppressed and it is not necessary to particularly secure the visual field. Therefore, any adverse reaction by injecting the physiological saline solution can be eliminated.

The eighth embodiment of the present invention shall be explained with reference to FIGS. 28 to 30.

Figure 28:
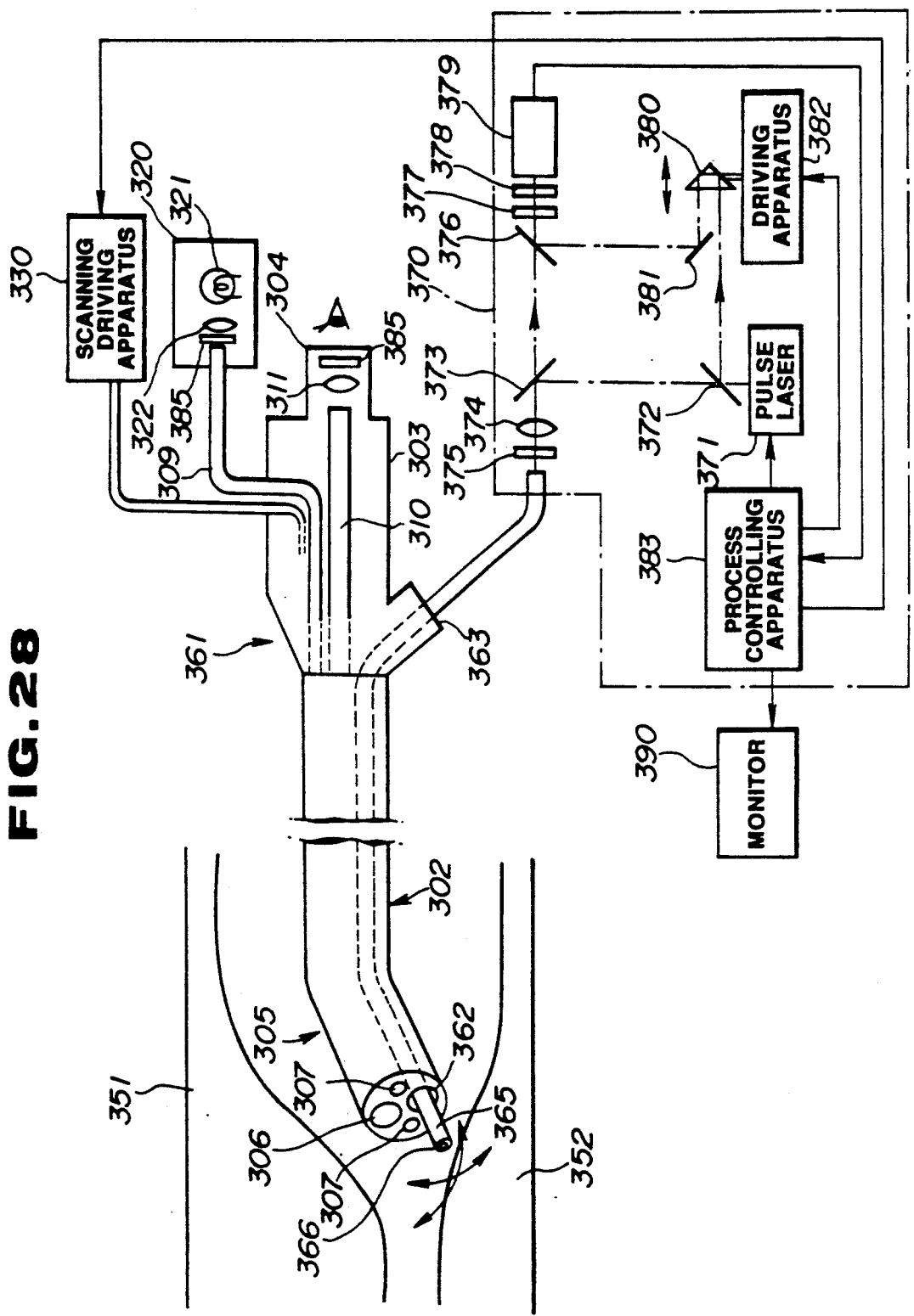
FIGS. 28 to 30 relate to the eighth embodiment of the present invention.

As shown in FIG. 28, an optical cross-sectioned vein endoscope apparatus of this embodiment comprises an endoscope 361, a light source apparatus 320 and scanning driving apparatus 330 connected with this endoscope 361, a probe 365 inserted through a channel in the above-mentioned endoscope 361, an optical cross-section photographing apparatus 370 connected with this probe 365 and a monitor 390 connected to the above-mentioned optical cross-section photographing apparatus 370.

The above-mentioned endoscope 361 comprises an elongate flexible insertable section 302 to be inserted into a vein 351, an operating section 303 provided on the base side of this insertable section 302 and a eyepiece section 304 provided at the rear end of this operating section 303. The above-mentioned insertable section 302 is provided in the tip part 305 with an observing window 306, illuminating window 307 and channel opening 10 362. The operating section 303 is provided with a channel inserting port 363. A channel connecting the above-mentioned channel opening 362 and channel inserting port 363 with each other is provided through the insertable section 302 and operating section 303.

The optical cross-section measuring probe 365 is inserted through the above-mentioned channel, has an optical fiber bundle 366 for radiating a measuring light to the measured position and receiving the reflected light from the measured position and is connected at the base end to the above-mentioned optical cross-section photographing apparatus 370.

The above-mentioned optical cross-section photographing apparatus 370 is provided with a pulse laser 371. The light emitted from this pulse laser 371 is separated into two parts by a beam splitter 372. The light having passed through this beam splitter 372 is reflected by a beam splitter 373, is condensed by a lens 374, passes through a filter (1) 375, enters the optical fiber bundle 366 of the above-mentioned probe 365 and is radiated to the measured position of such affected part 352 as, for example, an atheroma through this optical fiber bundle 366.

The reflected light from the measured position interior is led to the optical cross-section photographing apparatus 370 through the above-mentioned optical fiber bundle 366, passes through the above-mentioned filter (1) 375 and lens 374, passes further through the beam splitter 373 and a beam splitter 376 and enters a KDP 377 as a non-linear optical crystal.

On the other hand, the light emitted from the pulse laser 371 and reflected by the beam splitter 372 is reflected by the above-mentioned beam splitter 376 through a prism 380 and mirror 381 and enters the above-mentioned KDP 377 as a reference light. When the reflected light from the measured position and the above-mentioned reference light are input, the above-mentioned KDP 377 will generate a second harmonic wave. This second harmonic wave passes through a filter (2) 378 and is detected by a photo-multiplier tube 379. The above-mentioned prism 380 is moved by a driving apparatus 382 to vary the light path length of the above-mentioned reference light.

The intensity of the second harmonic wave generated by the above-mentioned KDP 377 is proportional to the integrated value of the product of the reflected light and reference light in case the above-mentioned reflected light and reference light are respectively made functions of time. Therefore, when the above-mentioned prism 380 is driven to vary the light path length of the reference light, the intensity of any time component of the reflected light from the measured position interior will be able to be detected by the photo-multiplier tube 379. Thus, the same as in the seventh embodiment, the time-analyzed waveform of the reflected light from the measured position interior can be detected. The output of the above-mentioned photo-multiplier tube 379 is input into a processing and controlling apparatus 383 which is to control the above-mentioned driving apparatus 382 and the scanning driving apparatus 330 for driving the tip part 305 of the endoscope 361.

Figure 30:
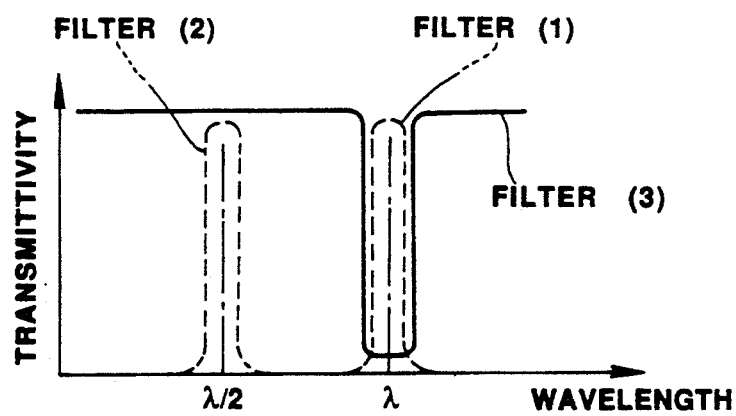

As shown in FIG. 30, in case the wavelength of the emitted light of the pulse laser 371 is represented by $\lambda$, in the characteristics, the above-mentioned filter (1) 375 will transmit a narrow band including the above-mentioned wavelength $\lambda$ and the filter (2) 378 will transmit a narrow band including the wavelength $\lambda/2$ of the second harmonic wave.

Also, in this embodiment, filters (3) 385 are provided respectively within the eyepiece section 304 of the endoscope 361 and within the illuminating light path of the light source apparatus 320. This filter (3) 385 has a characteristic of cutting a narrow band, including the above-mentioned wavelength $\lambda$, as shown in FIG. 30. When the above-mentioned filter (1) 375, filter (2) 377 and filter (3) 385 are provided, in the ordinary observation with the endoscope 361, the wavelength used in the optical cross-sectioned image observation will be cut, in the optical cross-sectioned image observation, the wavelength used in the ordinary observation with the endoscope 361 will be cut and the ordinary observation and optical cross-sectioned image observation will be able to be simultaneously made without influencing each other.

Figure 29:
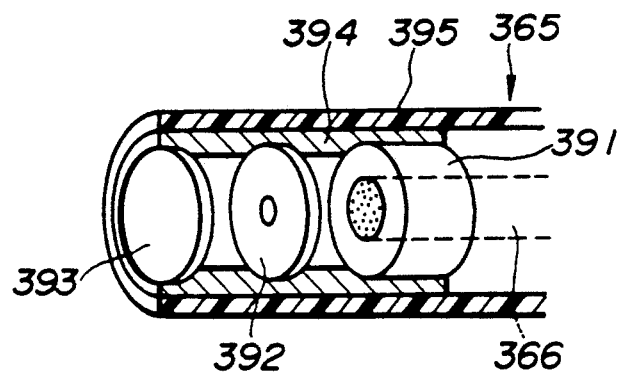

FIG. 29 shows an example of the formation of the tip part of the above-mentioned probe 365. In this example, such ultrasonic oscillator 391 as by a PZT is provided on the outer periphery of the tip part of an optical fiber bundle 366. Also, an aperture 392 and lens 393 are provided successively in front of the tip surface of the above-mentioned optical fiber bundle 366. These ultrasonic oscillator 391, aperture 392 and lens 393 are held and fixed within a cylindrical fixing member 394. The above-mentioned fixing member 394 and optical fiber bundle 366 are coated on the outer peripheries with a sheath 395. The above-mentioned ultrasonic oscillator 391 is driven by a driving apparatus, not illustrated, to constantly generate in a living body to be measured ultrasonic waves having a wave plane vertical to the ingress and egress direction of the light for the optical fiber bundle 366.

In this embodiment, the radiated light to the measured position and the reflected light from the measured position are transmitted through one optical fiber bundle 366, but may be through respective optical fiber bundles the same as in the seventh embodiment. Instead of the time-analytical light measuring means by using the KDP 377, a streak camera may be used as in the seventh embodiment.

The other formations, operations and effects are the same as in the seventh embodiment.

Figure 31:
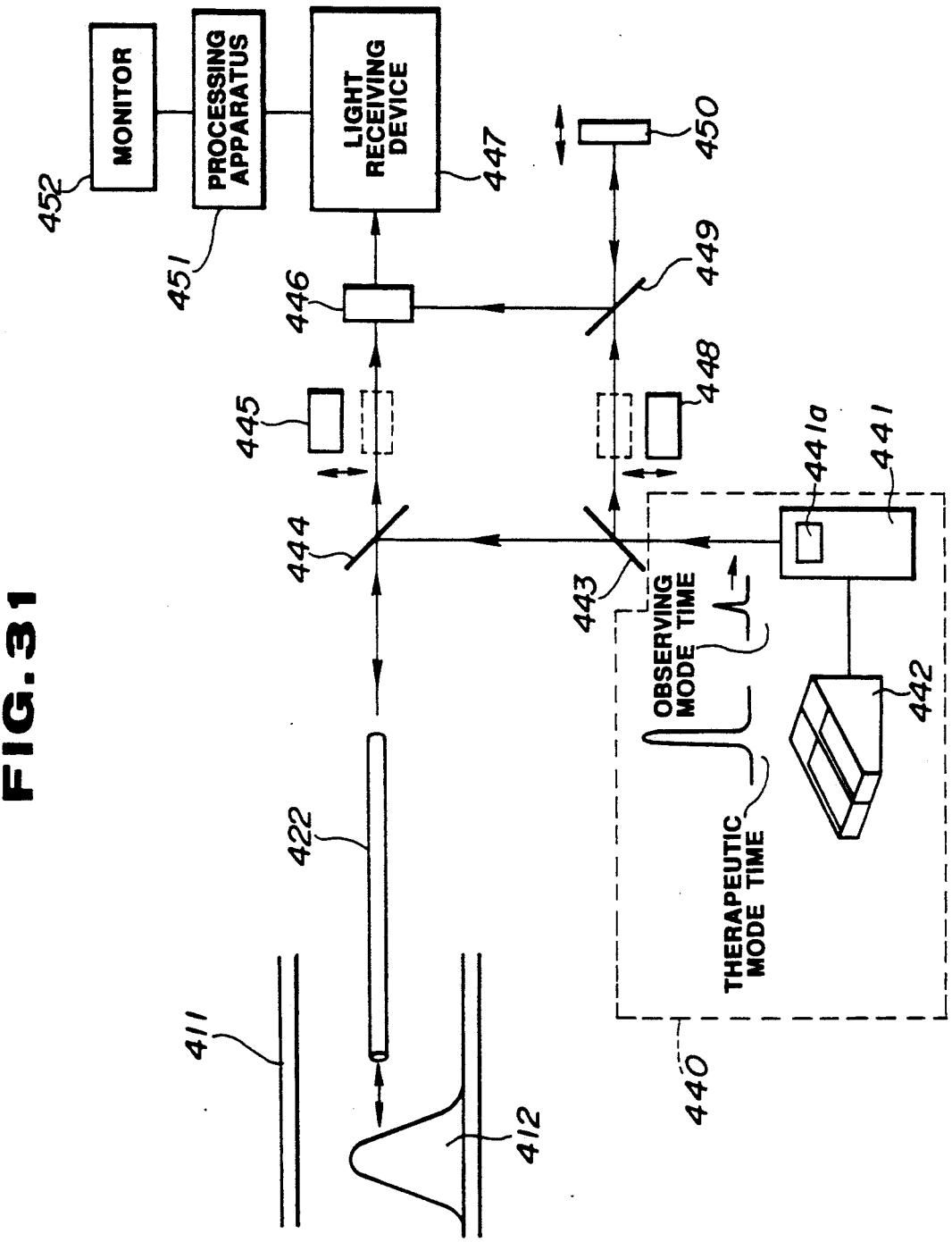
FIG. 31 is an explanatory diagram showing the formation of an essential part of the optical cross-sectioned vein endoscope apparatus of the ninth embodiment of the present invention.

FIG. 31 is an explanatory diagram showing the formation of an essential part of an optical cross-sectioned vein endoscope apparatus of the ninth embodiment of the present invention. In this embodiment, without requiring injection of a physiological saline solution, the visual field can be easily secured and the therapy can be efficiently made.

An endoscope apparatus of this embodiment comprises an endoscope 361 having a channel not illustrated the same as in the eighth embodiment, a light source apparatus 320 and a scanning driving apparatus 330. A laser probe 422 shown in FIG. 31 is inserted through the above-mentioned channel, is led into a vein and is connected at the rear end to a laser processing apparatus 440. This laser processing apparatus 440 comprises a laser oscillator 441 outputting an optical cross-sectioned image observing laser light and therapeutic laser light and a foot switch 442 controlling this laser oscillator. The above-mentioned laser oscillator 441 is provided with a Q switch 441a for generating pulse lights. The above-mentioned foot switch 442 is of a two-connected type so that, when one is trod, an observing mode will be made and a pulse light of an intensity adapted to the observation will be emitted from the laser oscillator 441 and, when the other of the foot switch 442 is trod, a therapeutic mode will be made and a pulse light having such energy as can destroy an atheroma will be emitted from the laser oscillator 441.

The emitted pulse light from the above-mentioned laser oscillator 441 passes through a half mirror 443, is reflected by a half mirror 444, enters the above-mentioned laser probe 422 and is radiated to such measured position as of an atheroma 412 through this laser probe 422. The reflected light from this atheroma 412 passes through the half mirror 444 through the laser probe 422 and enters a light receiving device 447 through a Kerr shutter 446. Also, the pulse light reflected by the above-mentioned half mirror 443 passes through a half mirror 449, is reflected by a reflecting mirror 450, is reflected by the above-mentioned half mirror 449 and opens the above-mentioned Kerr shutter 446.

The above-mentioned reflecting mirror 450 is moved in the optical axial direction by a driving apparatus not illustrated to vary the light path length of the pulse light for opening the Kerr shutter. A light attenuator 445 is removably provided in the light path between the half mirror 444 and Kerr shutter 446 and a light attenuator 448 is removably provided in the light path between the half mirrors 443 and 449 so that the respective light attenuators 445 and 448 may be inserted into and removed from the light path in response to the switching of the above-mentioned foot switch 442 by a driving apparatus not illustrated.

The output signal of the above-mentioned light receiving device 447 is processed by a processing apparatus 451 to form an optical cross-sectioned image of the measured position. The optical cross-sectioned image formed by this processing apparatus 451 is displayed in a monitor 452.

The observing and therapeutic operations by using the laser probe 422 shall be explained below.

First of all, when an observing mode is set with the foot switch 442, the light attenuators 445 and 448 will be retreated from the light path as shown by the solid lines in FIG. 31 and the pulse light of the intensity adapted to the observation will be emitted from the laser oscillator 441 and will be radiated to such measured position as of the atheroma 312 through the half mirrors 443 and 444 and laser probe 422.

The reflected light from the interior of this measured position is received by the light receiving device 447 through the laser probe 422, half mirror 444 and Kerr shutter 446. When the reflecting mirror 450 is moved to vary the light path length of the pulse light opening the Kerr shutter 446, the intensity of any time component of the reflected light from the interior of the measured position will be able to be detected.

Thus, the same as in the seventh and eighth embodiments, the time-analyzed waveform of the reflected light from the measured position interior can be detected. The same as in the eighth embodiment, when the measured position is scanned by driving the tip part of the insertable section 305 of the endoscope 361 and the time-analyzed waveform in each position is detected and is processed by the processing apparatus 451, an optical cross-sectioned image of the measured position will be obtained. This optical cross-sectioned image is displayed in the monitor 452.

When a therapeutic mode is set with the foot switch 442, the light attenuators 445 and 448 will be inserted in to the light path as shown by the broken lines in FIG. 31 and a pulse light of the intensity adapted to the therapy will be emitted from the laser oscillator 441 and will be radiated to such therapeutic position as of the atheroma 412 through the half mirrors 443 and 444 and laser probe 422 to make a therapy of the therapeutic position. The reflected light from the interior of the therapeutic position is attenuated to be of substantially the same intensity as of the reflected light at the time of the observing mode through the laser probe 422, half mirror 444 and light attenuator 445 and enters the Kerr shutter 446.

The pulse light reflected by the half mirror 443 is attenuated to be of substantially the same intensity as the intensity at the time of the observing mode and enters the Kerr shutter 446 through the half mirror 449, reflecting mirror 450 and half mirror 449. Thus, even at the time of the therapeutic mode, the intensity of the light entering the Kerr shutter 446 and light receiving device 447 will not be different from that at the time of the observing mode and therefore the optical cross-sectioned image will be able to observed while undergoing the therapy. The Kerr shutter 446 and light receiving device 447 can be prevented from being destroyed and the picture quality can be prevented from varying in the observing mode and therapeutic mode.

According to the embodiment, the illuminating light source used in the conventional endoscope is not required.

By the way, the observing laser oscillator and therapeutic laser oscillator may be separately provided so as to be switched over to each other in response to the mode.

By the way, this embodiment can be applied also to industrial uses.

The other formations, operations and effects are the same as in the seventh embodiment.

By the way, in the above-mentioned seventh to ninth embodiments, for example, instead of the photo-pulse radiated to the measured object, a modulated light may be used.

According to the seventh to ninth embodiments, by leading the insertable section to the measured object in such fine part as a vein, the optical cross-sectioned image of this measured object can be obtained and therefore there is an effect that the internal form of such fine part as a vein can be detected.

An optical three-dimensional image observing apparatus for forming a three-dimensional image from an optical cross-sectioned image of a measured object shall be explained in the following. This embodiment relates to an optical three-dimensional image observing apparatus whereby a three-dimensional structure of an examined body interior can be accurately and easily caught and not only a structural measurement but also a functional measurement can be made.

Figure 32:
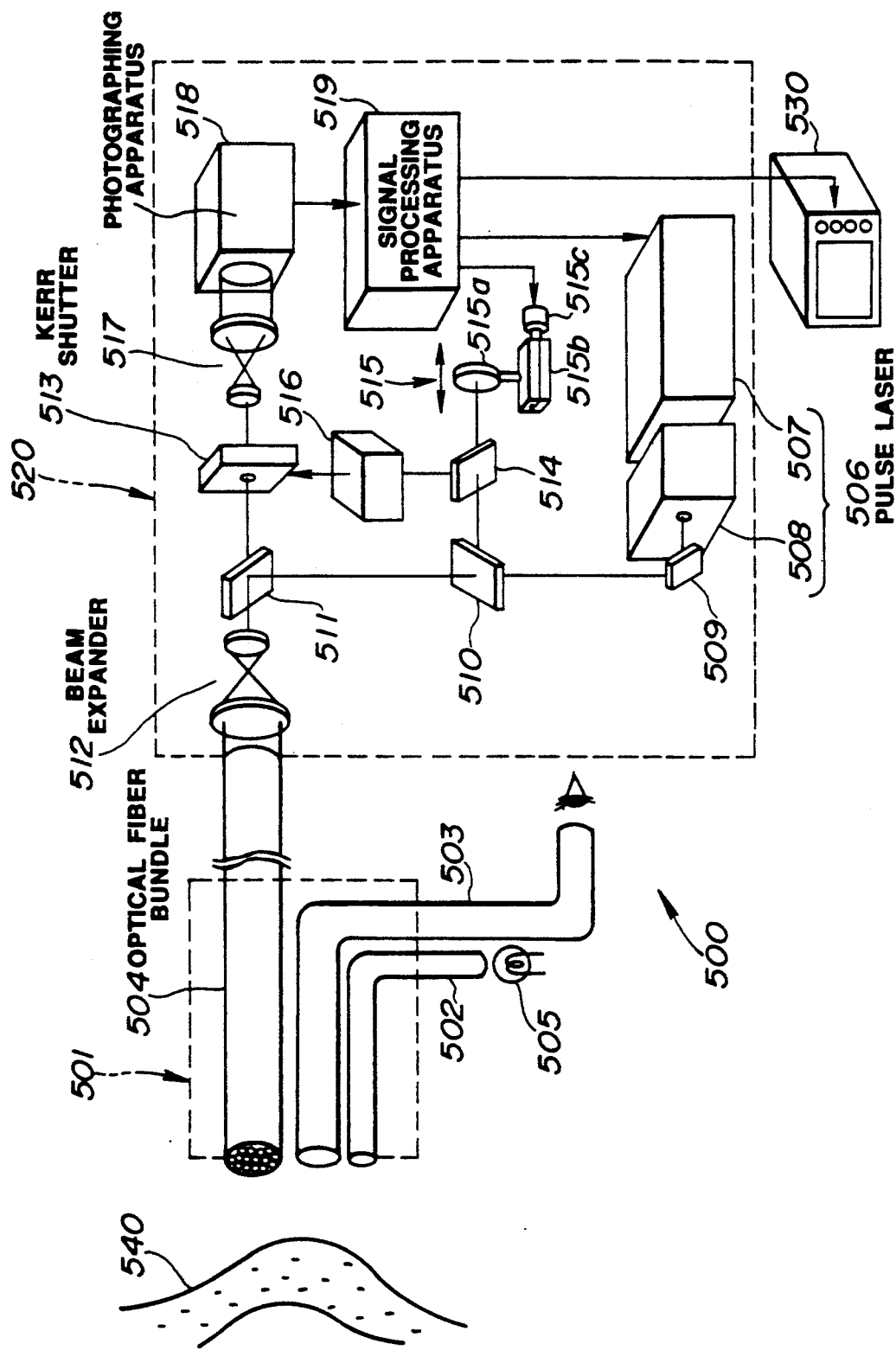
FIGS. 32 to 42 relate to the tenth embodiment of the present invention.

As shown in FIG. 32, an optical three-dimensional image observing apparatus 500 comprises an endoscope 501, an optical three-dimensional image processing apparatus 520 connected with this endoscope 501 and a monitor 530 connected to this optical three-dimensional image processing apparatus 520.

In the above-mentioned endoscope 501, a light guide 502 and image guide 503 for observing the surface part of an examined body interior and an optical fiber bundle 504 connected to the above-mentioned optical three-dimensional image processing apparatus 520 are inserted through an elongate flexible insertable section to be inserted into the examined body interior.

The above-mentioned light guide 502 transmits an illuminating light entering through a condensing lens, not illustrated, from a light source 505 and radiates it to an observed position through a light distributing lens, not illustrated, fitted to the tip of the above-mentioned insertable section.

The above-mentioned image guide 503 leads an optical image of the observed position formed by an objective lens, not illustrated, at the tip of the above-mentioned insertable section so as to be able to be observed with a naked eye through an eyepiece lens, not illustrated, provided on the rear end surface.

The above-mentioned optical three-dimensional image processing apparatus 520 is provided with a pulse laser 506 as a photo-pulse generating means. This pulse laser 506 is formed of an Nd:YAG laser 507 and dye laser 508. The emitted light from the above-mentioned Nd:YAG laser 507 is radiated to a dye (for example, Rhodamine 6G) within the above-mentioned dye laser 508 and the light emitted from this dye laser 508 is reflected by a mirror 509 and is separated into two lights by a beam splitter 510.

The light having passed through the above-mentioned beam splitter 510 is reflected by a beam splitter 511, is then expanded to be a parallel light of the same diameter as of the above-mentioned optical fiber bundle 504 from the fine beam light by a beam expander 512, enters the above-mentioned optical fiber bundle 504 as uniformly diffused and is radiated to such measured object as an affected part 540 through this optical fiber bundle 504.

The reflected light reflected by this affected part 540 is led by the above-mentioned optical fiber bundle 504, passes through the beam splitter 511 through the above-mentioned beam expander 512 from this optical fiber bundle 504 and enters a Kerr shutter 513 which acts as an optical opening and closing means.

On the other hand, the light emitted from the above-mentioned dye laser 508 and reflected by the above-mentioned beam splitter 510 passes through a beam splitter 514 and is reflected by a mirror 515a of a delaying mirror apparatus 515. Further, the light reflected by this mirror 515a is reflected by the above-mentioned beam splitter 514 and enters a driving apparatus 516 comprising a photo-diode or the like and the above-mentioned Kerr shutter 513 is opened by an electric signal from this driving apparatus 516.

The above-mentioned delaying mirror apparatus 515 is provided with a movable stage 515b on which the above-mentioned mirror 515a is fixed so that, when this movable stage 515b is driven by a stepping motor 515c to move in the optical axial direction, the light path length to the above-mentioned driving apparatus 516 will be varied.

The light having passed through the above-mentioned Kerr shutter 513 enters an imaging apparatus 518 of a high sensitivity combining a video multiplying tube and SIT camera through a beam expander 517 and the output signal from this imaging apparatus 518 is processed in a signal processing apparatus 519.

In the above-mentioned imaging apparatus 518 and signal processing apparatus 519, the stepping motor 515c of the above-mentioned delaying mirror apparatus 515 is controlled by the above-mentioned signal processing apparatus 519 and a three-dimensional image is formed on the basis of the cross-sectioned image of the measured position detected by the above-mentioned imaging apparatus 518 and is displayed in the above-mentioned monitor 530. The above-mentioned signal processing apparatus 519 variably controls the gain for the signal corresponding to the cross-sectioned image output from the imaging apparatus 518 in response to the variation of the light path length by the stepping motor 515c.

The observation of the three-dimensional image of the examined body interior by this optical three-dimensional image observing apparatus shall be explained in the following.

Figure 33:
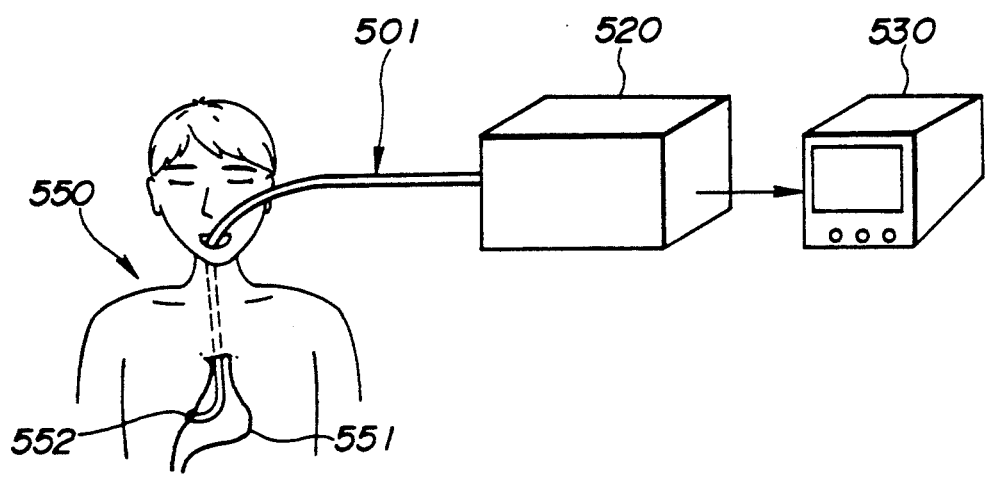

As shown in FIG. 33, for example, in the case of observing a three-dimensional image in an organ 551 of a human body 550, first of all, the insertable section of the endoscope 501 will be inserted into the body cavity interior of the human body 550 and the tip part is opposed to such affected part as a cancer or ulcer.

Then, a light of several ten picoseconds is generated from the Nd:YAG laser 507 by the pulse laser 506 within the optical three-dimensional image processing apparatus 520 and is radiated to excite the dye within the dye laser 508 and a photo-pulse of a very short time width of several picoseconds is emitted from this dye laser 508, is expanded by the expander 512 through the mirror 509 and beam splitters 510 and 511, uniformly enters the optical fiber bundle 504 and is radiated like a surface to the affected part 552 which is a measured object.

When the radiated photo-pulse is reflected by the surface and deep of the affected part 552, the reflected photo-pulse will be led to the above-mentioned optical three-dimensional image processing apparatus 520 from the above-mentioned optical fiber bundle 504, will be converged again into a fine beam light by the above-mentioned beam expander 512, will pass through the beam splitter 511 and will enter the Kerr shutter 513.

At this time, the photo-pulse emitted form the above-mentioned dye laser 506 and separated by the beam splitter 510 will be led to the beam splitter 514, mirror 515a and beam splitter 514, the above-mentioned Kerr shutter 513 will be opened for a predetermined time by a signal photoelectrically converted by this driving apparatus 516 and the reflected light having passed through this Kerr shutter will be led to the imaging apparatus 518 through the beam expander 517.

Figure 34:
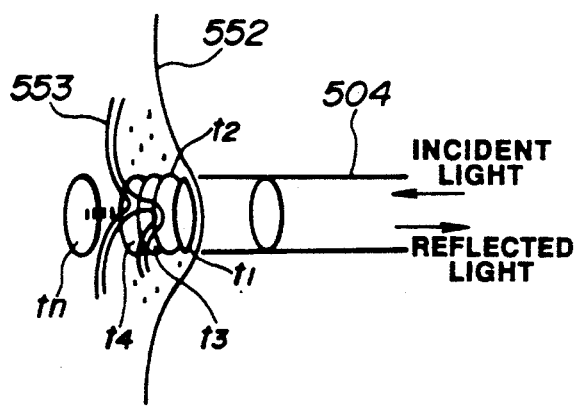
Figure 35:
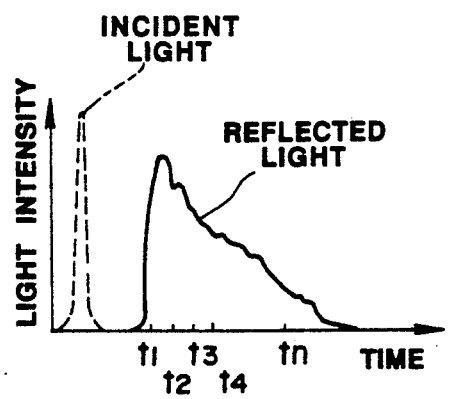

The above-mentioned Kerr shutter opening timing is set by varying the light path length by moving the mirror 515a of the above-mentioned delaying mirror apparatus 515 and controlling the time when the photo-pulse arrives at the above-mentioned driving apparatus 516. That is to say, as shown in FIG. 34, the times 5a, t2, t3, t4, ... and tn when the reflected light arrives at the above-mentioned Kerr shutter 513 against the incident light upon the affected part 552 are different depending on the tissue depth of the affected part 552 and therefore, as shown in FIG. 35, against the incident light shown by the broken line, the intensities of the reflected light from the respective points within the tissue can be obtained from such time-analyzed waveform, as is shown by the solid line.

Figure 36:
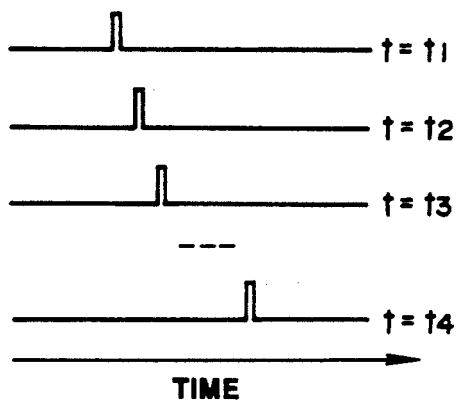

Therefore, when the above-mentioned Kerr shutter 513 opening timing is set at each of the times t1, t2, t3, t4, ... and tn, as shown in FIG. 36, the reflected photo-pulses from the respective points within the tissue led by the above-mentioned optical fiber bundle 504 are transmitted to the above-mentioned imaging apparatus 518 and the reflected light intensity is analyzed, at each opening timing of the above-mentioned Kerr shutter 513, an optical cross-sectioned image of the affected part 552 corresponding to the photo-pulse radiating plane by the above-mentioned optical fiber bundle 504 will be able to be detected.

Figure 37:
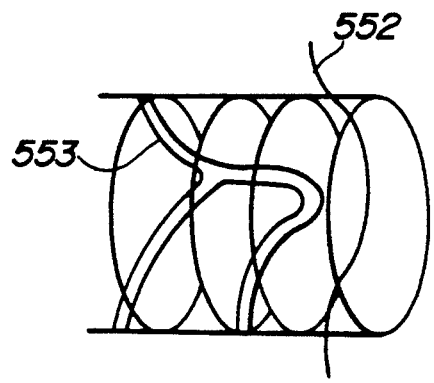

When the optical cross-sectioned image at each of these times t1, t2, t3, t4, ... and tn is processed by the above-mentioned signal processing apparatus 519, as shown in FIG. 37, a three-dimensional image including a vein 553 of the tissue interior of the affected part 552 will be obtained and will be able to be displayed in the monitor 530.

Thereby, the structure of the tissue interior can be caught accurately and easily and the internal state of the affected part 552 can be accurately diagnosed. Further, when the measurement is repeated by varying the wavelength of the dye laser 508 of the above-mentioned pulse laser 506 and the operation is made between the respective cross-sectioned images obtained by the photo-pulses of different wavelengths, such physiological composition as, for example, the degree of oxygen saturation within the above-mentioned vein 554 will be able to be displayed in three dimensions. Therefore, not only the structure within the tissue but also the state of the metabolic function can be caught and an integral diagnosis can be made.

Now, in this three-dimensional image observing apparatus, when a dispersed light from the affected part 552 enters the above-mentioned imaging apparatus 518, it will be considered a noise which deteriorates the image. Therefore, it is necessary to suppress the above-mentioned dispersed light and extract only the straight proceeding component.

Figure 38:
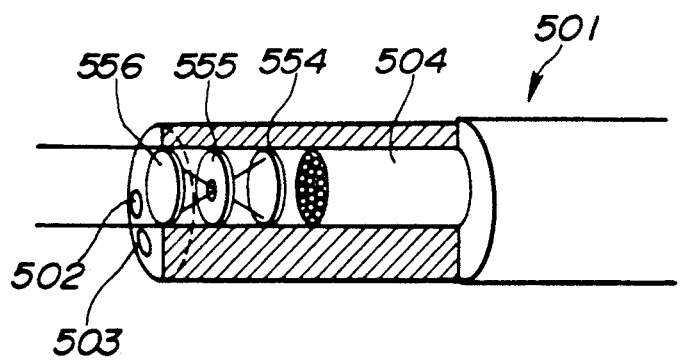
Figure 39:
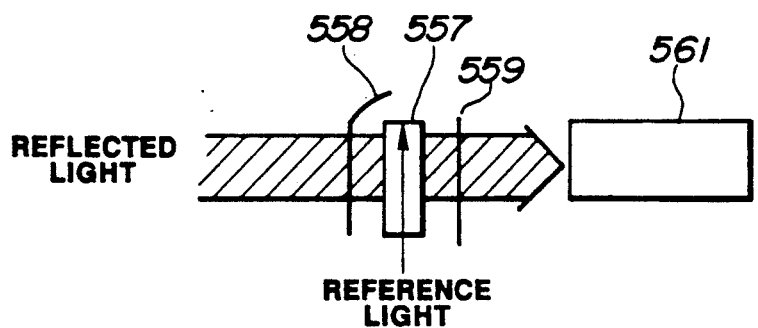

FIG. 38 shows an example of a dispersed light suppressing means as provided in the tip part of the endoscope 501 wherein is provided a collimator in which a lens 554, aperture (diaphragm) 555 and lens 556 are successively arranged on the front surface of the above-mentioned optical fiber bundle 504 to limit such excess light as a dispersed light. Without providing the above-mentioned collimator, even by making the above-mentioned optical fiber bundle of single mode fibers, the dispersed light can be effectively suppressed. The optical opening and closing means may consist of the above-described Kerr shutter 513 utilizing the double refraction of carbon disulfide ($CS_2$) or nitrobenzene. FIG. 39 illustrates an example. The reference numerals 558 and 559 represent polarizers intersecting at right angles with each other so that, only when the $CS_2$ produces a double refraction will the reflected light pass through them. It is a photo-shutter wherein the reference light enters $CS_2$ to generate a double refraction.

In order to effectively utilize the optical three-dimensional image observing apparatus of the present invention, it is effective to make the observed region wide angled. Such an example shall be explained below.

Figure 40:
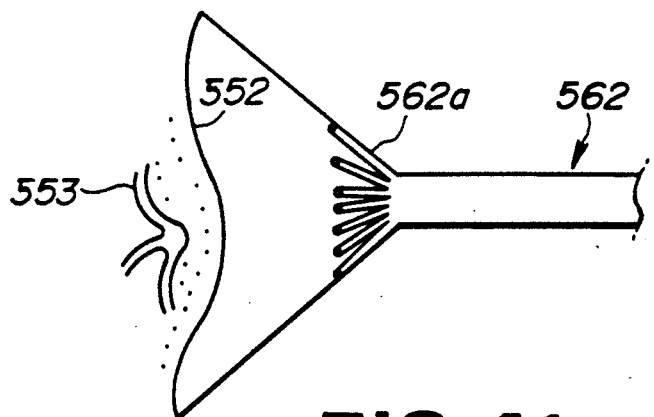

In FIG. 40, by radially expanding respective optical fibers 562a forming an optical fiber bundle 562 in the tip part of this optical fiber bundle, the three-dimensional image of the interior can be observed over the wide region on the periphery of the affected part 552.

Figure 41:
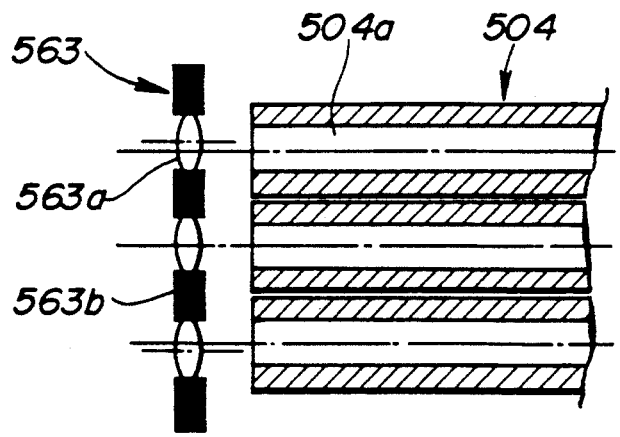

In this case, when an ordinary lens is arranged on the front surface of the above-mentioned optical fiber bundle 504, the observed region will be able to be viewed in a wide angle but, when such lens array 563 as is shown in FIG. 41 is used, it will be able to be more effectively viewed in a wide angle.

Figure 42:
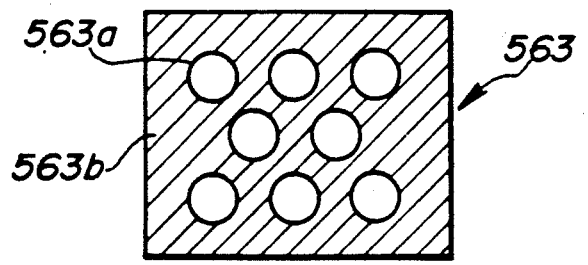

In the above-mentioned lens array 563, the respective lenses 563a are arranged at a pitch larger than the pitch between the respective optical fibers 504a forming the above-mentioned optical fiber bundle 504 and more eccentrically on the periphery and, as shown in FIG. 42, the light intercepting part 563b between the respective lenses 563a is formed of black oxidized glass or the like.

When this lens array 563 is arranged as opposed to the front surface of the above-mentioned optical fiber bundle 504, the observed region will be able to be viewed in a wide angle and, when the lens diameters of the above-mentioned respective lenses 563a and the thickness of the above-mentioned light intercepting part 563b are properly set to reduce the number of entrance apertures or the F value, even in case the above-mentioned optical fibers 504a are multi-mode fibers, the number of entrance modes will be able to be reduced to suppress the dispersion of the light within the fiber when the light is transmitted.

Further, when the distance between the above-mentioned lens array 563 and the end surface of the above-mentioned optical fiber bundle 504 is properly set, the expansion of the light entering the respective optical fibers 504a will be able to be reduced, therefore the expanding direction of the measured surface will be able to be separated and the cross-talk of the information of the respective optical fibers 504a with each other will be able to be avoided.

According to this tenth embodiment, as a three-dimensional image can be obtained from an optical cross-sectioned image of a measured object, there are effects that the form of the measured object interior can be caught accurately and easily and the integral measurement including not only the structural measurement but also the functional measurement can be made.

An endoscope apparatus whereby a normal cross-sectioned image is obtained by removing a false image caused in the optical system shall be explained in the following.

This is to dissolve the defect that, in the case of an endoscope apparatus for obtaining a cross-sectioned image by using, for example, a streak camera, in addition to the inherent reflected light from the observed part, a laser light will be reflected on many end surfaces of the optical system, particularly, the relay optical system or the like and thus so many reflected lights will enter the streak camera that a normal cross-sectioned image will not be obtained.

The 11th embodiment of the present invention shall be explained in the following with reference to FIGS. 43 and 44.

Figure 43:
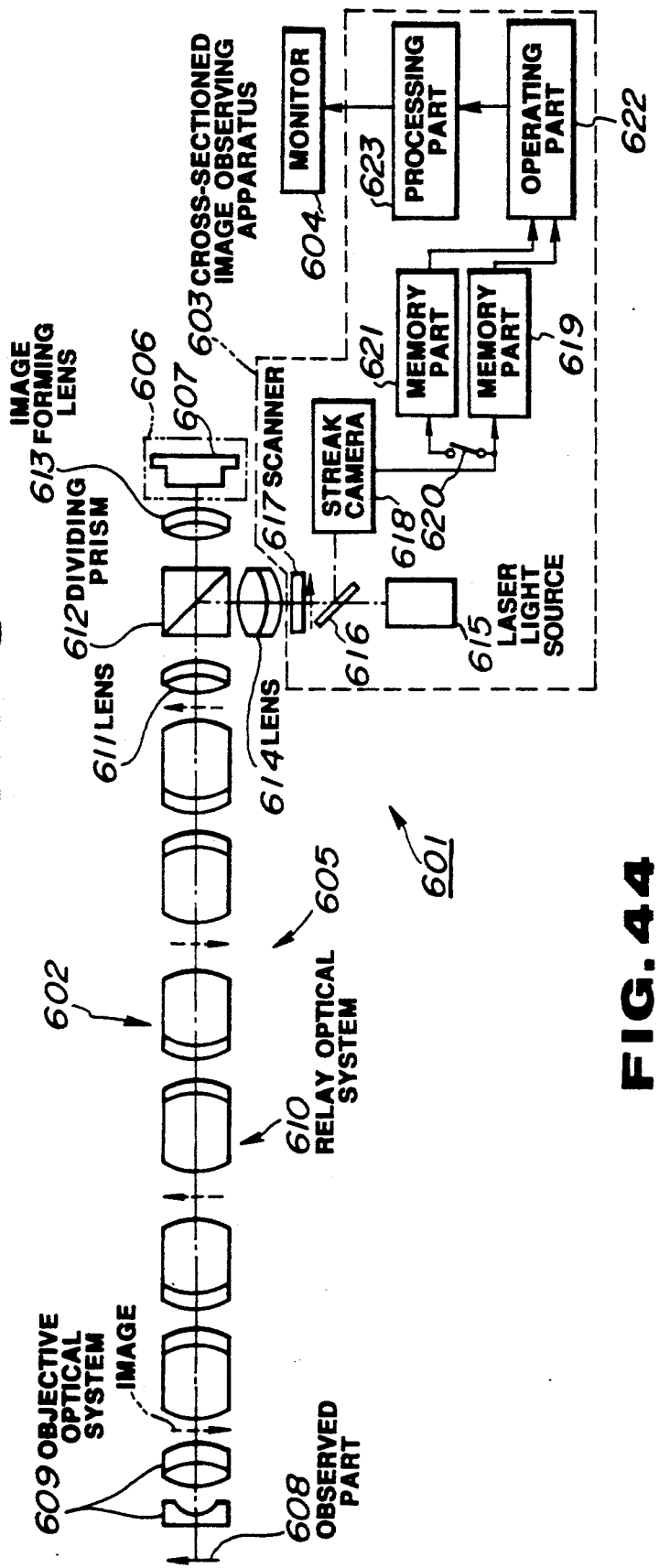
FIGS. 43 and 44 relate to the 12th embodiment of the present invention.
Figure 44:
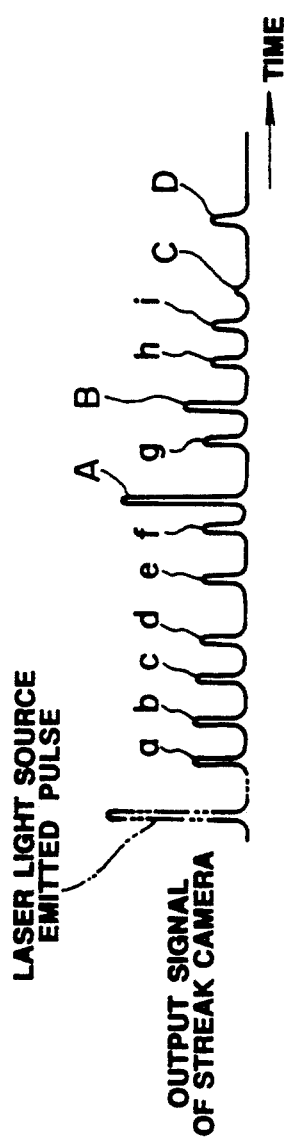

A rigid electronic endoscope apparatus 601 shown in FIG. 43 comprises a rigid electronic endoscope 602 to be inserted into a body cavity of an examinee to observe the body cavity interior, a cross-sectioned image observing apparatus 603 for obtaining a cross-sectioned image of the body cavity interior, a monitor 604 for displaying the cross-sectioned image and a light source apparatus, not illustrated, for emitting an illuminating light for obtaining a surface image of the body cavity interior.

The above-mentioned rigid electronic endoscope 602 comprises a fine diameter rigid insertable section 605 to be inserted into the body cavity and an operating section 606 provided at the rear end of this insertable section 605. The above-mentioned insertable section 606 is internally provided with such optical system as of a later described lens, prism and relay optical system as a light transmitting means.

A light guide fiber bundle, not illustrated, is connected at the entrance end to the above-mentioned light source and is inserted through the above-mentioned operating section 606 and insertable section 605 so that an observing light may be radiated to an observed part 608 from an emitting end provided at the tip of the insertable section 605.

The reflected light from the observed part 608 enters an objective optical system 609 internally provided at the tip of the above-mentioned insertable section 605 and further forms an image on the imaging surface of a solid state imaging device 607 internally provided in the operating section 606 through a relay optical system 610, lens 611, dividing prism 612 and image forming lens 613 on the same optical axis internally provided in the insertable section 605.

The above-mentioned cross-sectioned image observing apparatus 603 has a laser light source 615 emitting a laser light necessary to obtain a cross-sectioned image as a pulse light of a pulse width, for example, of a picosecond unit and is provided on the optical axis of the laser light with a half mirror 616 passing this laser light and a scanner 617 as a scanning means scanning the passing laser light. A lens 614 and the above-mentioned dividing prism 612 internally provided in the above-mentioned insertable section 605 are arranged on the optical axis of this laser light which intersects at right angles with the optical axis of the above-mentioned relay optical system 610. The laser light emitted from the laser light source 615 is scanned by the scanner 617 through the half mirror 616, enters 10 the lens 614 of the above-mentioned insertable section, is reflected by the above-mentioned dividing prism 612 and is radiated to the observed part 608 through the relay optical system 610 and objective optical system 609. The returning light reflected by the surface and interior of the observed part 608 is reflected by the half mirror 616 through the objective optical system 609, relay optical system 610, lens 611, dividing prism 612 and lens 614. A streak camera 618 as a detecting means for time-analytically detecting the returning light is arranged in the light part of the reflected returning light.

The above-mentioned cross-sectioned image observing apparatus 603 comprises a memory part 619 time-serially memorizing the returning light from the observed part 608 output from the above-mentioned streak camera 618 and all information signals, a memory part 621 as a recording means memorizing through a switch 620 the reflected information signals corresponding to the reflected lights reflected by a plurality of end surfaces of such optical system as of the lenses 611 and 614 output from the above-mentioned streak camera 618 and a processing part 623 converting the observed information signal of the operating part 622 to a cross-sectioned image signal. The above-mentioned monitor 604 is connected to this processing part 623 and displays the cross-sectioned image.

The operation of this embodiment shall be explained with reference to FIGS. 43 and 44.

First of all, in order to prevent the return of light from the observed part 608 or the like, the tip of the non-rigid electronic endoscope 602 is directed, for example, away from any object and the switch 620 of the cross-sectioned image observing apparatus 603 is set on. In this state, when a laser light is emitted from the laser light source 615, the laser light will pass through the half mirror 616 and will be scanned at a high speed by the scanner 617. The scanned light from the scanner 617 is reflected by the dividing prism 612 through the lens 614 and is radiated from the emitting end of the objective optical system 609 further through the relay optical system 610. Because there is no reflecting object, the radiated scanned light will not return as a reflected light. On the other hand, the scanned light will produce reflected light rays on the respective end surfaces while passing through the lens 614, dividing prism 612, lens 611, relay optical system 610 and objective optical system 609. These reflected light rays follow a reverse course from the scanned light, are reflected by the half mirror 616 and enter the streak camera 618. The arriving time of the light entering the streak camera 618 is proportional to the position in which the scanned light is reflected, that is, to the light path length. Therefore, the larger the distance from the streak camera, the later the arriving time. The streak camera 618 time-serially analyzes the reflected light rays different in the entering time and detects them as a train of pulse signals. The amplitude of such pulse signal is proportional to the intensity of the entering light. The memory part 621 time-serially memorizes the intensity of the pulse signal train of the reflected lights as of the reflected information signals.

Then, the switch 620 of the cross-sectioned image observing apparatus 603 is set off and the insertable section 605 of the rigid electronic endoscope 602 is inserted into the body cavity. In this state, when a laser light is emitted from the laser light source 615, the laser light will pass through the half mirror 616 and will be scanned at a high speed by the scanner 617. The scanned light from the scanner 617 is reflected by the dividing prism 612 through the lens 614 and is radiated to the observed part further through the relay optical system 610 and objective optical system 609. The radiated scanned light passes through the interior of the observed part and is reflected by the surface and internal tissue of the observed part to be a returning light. This returning light is reflected by the half mirror 616 through the objective optical system 609, relay optical system 610, lens 611, dividing prism 612 and lens 614 and enters the streak camera 618 together with the reflected light from the above-mentioned optical system. The arriving time of the entering returning light corresponds to the reflecting position in the depth direction of the observed part. The deeper the reflecting surface, the later the arriving time. Thus, the farther from the streak camera 618 the reflecting position (that is, the longer the light path length), the later the returning light and reflected light. The streak camera 618 time-analytically analyzes the returning light and reflected light different in the entering time, detects them as a train of pulse signals and outputs it to the memory part 619. FIG. 44 shows as an example a pulse signal train output from the streak camera 618. The laser light of one pulse emitted from the laser light source 615 is shown by the two-point chain line in the diagram. The reference symbols A to D in the diagram represent pulse signals 10 produced by the returning lights from the surface and interior of the observed part 608 of the laser light of one pulse. The reference symbols a to i in the diagram represent pulse signals produced by the reflected lights of the optical system. The arriving times of the returning lights A to D correspond to the depths of the reflecting surfaces within the living body. Also, the amplitude of the pulse signal corresponds to the optical property of the reflecting surface within the above-mentioned living body. The deeper the position of the reflecting surface of the living body, the lower the amplitude of the pulse signal. It is also shown that the reflected lights g to i are multiplexly reflected on the end surface of the optical system and are later in the arriving time than the returning light rays from the living body.

The memory part 619 time-serially memorizes the train of pulse signals in which the returning lights and reflected lights are present as mixed and outputs it to the operating part 622. The operating part 622 compares and removes for each simultaneous information all the information signals (the signals corresponding to the returning lights A to D and reflected lights a to i) memorized in the memory part 619 and the reflected information signals (the signals corresponding to the reflected lights a to i) of the above-mentioned memory part 621 and outputs them to the processing part 623 as the observed information signals corresponding to the returning lights A to D from the observed part. This operating part 622 removes the reflected information signals of the memory part 621 from all the information signals output successively from the memory part 619 10 and outputs them to the processing part 623 which converts the observed information signals corresponding to one scanned part of the scanner 617 to cross-sectioned image signals and outputs them to the monitor 604. The monitor 604 receives the cross-sectioned image signals and displays the cross-sectioned images.

In this embodiment, the reflected light rays from the relay optical system 610 and the like and the returning lights from the observed part as mixed enter the streak camera 618 but the reflected light part only is removed by the operating part 622. Therefore, the monitor 604 will not reproduce any false image caused by the relay optical system 610 and the like and can display normal cross-sectioned images. The surface image of the observed part can be also obtained by the solid state imaging device 607 or the like.

The rigid electronic endoscope shown in the embodiment may be used for a resectoscope used in the urinary organ field.

Also, in this embodiment, the rigid electronic endoscope is exemplified but a flexible endoscope or the like may be also used. In such case, the reflected lights from the end surfaces of the optical fibers and lenses will be removed.

The streak camera is exemplified as a detecting means but, in such apparatus using a non-linear optical crystal as a Kerr shutter or KDP, the lights may be time-analytically detected.

According to this 11th embodiment, even if the light in which the plurality of reflected light rays from the light transmitting means and the returning lights from the observed part are present as mixed may enters such detecting means as a streak camera, the reflected information signal part memorized in advance by the memorizing means will be able to be removed from all the information signals by the operating means and therefore there are effects that any false image caused by the light transmitting means will not be reproduced and a normal cross-sectioned image of the object observed part can be obtained.

The present invention is not limited to the above-described embodiments. For example, different embodiments can be formed by partly combining the various embodiments and also belong to the present invention.

What is claimed is:

1. An examined body interior information observing apparatus comprising:
   a photo-pulse generating means for generating light energy in the form of photo-pulses for observing the interior of an examined body;
   a time-analytical reflected light detecting means for time-analytically measuring in response to a depth from a surface of the examined body light energy emitted from said photo-pulse generating means and reflected within said examined body to produce an output signal; and
   a detection sensitivity varying means for varying detection sensitivity so that a level of at least the output signal of said time-analytical reflected light detecting means may vary in response to said light energy reflected from different depths within said examined body.

2. An examined body interior information observing apparatus according to claim 1 wherein said detection sensitivity varying means inputs into said time-analytical reflected light detecting means a detection sensitivity controlling signal for controlling the detection sensitivity of said time-analytical reflected light detecting means.

3. An examined body interior information observing apparatus according to claim 1 further comprising an objective optical system for radiating/condensing said photo-pulses from said photo-pulse generating means to said examined body and said detection sensitivity varying means varies a focus position of said objection optical system in response to said light energy reflected from the depth of said examined body.

4. An examined body interior information observing apparatus according to claim 1 wherein said time-analytical reflected light detecting means has a beam splitting means for branching said photo-pulses emitted from said photo-pulse generating means into two pluses consisting of a first photo-pulse proceeding to said examined body surface and a second photo-pulse used as a reference, a delaying means for delaying said second photo-pulse branched by said beam splitting means and a photo-mixing means for photo-mixing a reflected light energy of said first photo-pulse reflected on a side of said examined body and returning said second photo-pulse delayed by said delaying means and substantially extracting only a reflected component of said first photo-pulse which is synchronized by said time-analytical reflected light detecting means with an input minute time of said second photo-pulse to produce a photo-mixed output light.

5. An examined body interior information observing apparatus according to claim 4 wherein said time-analytical reflected light detecting means has a photo-electrically converting and amplifying means for outputting the output light of said photo-mixing means as an amplified electric signal.

6. An examined body interior information observing apparatus according to claim 5, wherein said detection sensitivity varying means outputs a detection sensitivity controlling signal for controlling the level of the output signal of said photoelectrically converting and amplifying means in response to the above mentioned depth.

7. An examined body interior information observing apparatus according to claim 5 wherein said detection sensitivity varying means applies to said photoelectrically converting and amplifying means a detection sensitivity controlling signal which exponentially increases the detection sensitivity of said photoelectrically converting and amplifying means with said depth.

8. An examined body interior information observing apparatus according to claim 5 wherein said photoelectrically converting and amplifying means is a photo-multiplier tube and said detection sensitivity varying means applies a controlling signal controlling a photomultiplying rate of said photo-multiplier tube.

9. An examined body interior information observing apparatus according to claim 5 wherein said photo-mixing means has a neutral density filter arranged in front of said photoelectrically converting and amplifying means and having a transmittivity distributed in a peripheral direction and motor for rotating and driving said neutral density filter in the peripheral direction and said detection sensitivity varying means controls a rotation of said motor in response to said depth.

10. An examined body interior information observing apparatus according to claim 4 wherein said photo-mixing means has a transmitting filter for selectively transmitting a predetermined wavelength range component in the photo-mixed output light.

11. An examined body interior information observing apparatus according to claim 10 wherein said photo-mixing means has a photoelectrically converting and amplifying means outputting as an electric signal said output light passed through said filter.

12. An examined body interior information observing apparatus according to claim 4 wherein said delaying means includes a mirror oriented to be opposed to said beam splitting means for delaying said second photo-pulse from entering a side of said photo-mixing means for a time corresponding to the distance from said beam splitting means to said mirror in said delaying means.

13. An examined body interior information observing apparatus according to claim 12 wherein said delaying means has an adjusting means for varying the distance between said mirror and said beam splitting means.

14. An examined body interior information observing apparatus according to claim 4 wherein said photo-mixing means includes a non-linear optical device having a non-linear input and output characteristic for entering light energy.

15. An examined body interior information observing apparatus according to claim 1 wherein said time-analytical reflected light detecting means has a beam splitting means for branching each said photo-pulse emitted from said photo-pulse generating means into two photo-pulses consisting of a first photo-pulse proceeding to said examined body surface and a second photo-pulse, a delaying means for delaying said second photo-pulse branched by said beam splitting means and a shutter means for selectively extracting a reflected light component of said first photo-pulse synchronized by said time-analytical reflected light detecting means with the timing of a reference signal corresponding to a reflected light of said first photo-pulse reflected from a side of said examined body and said second photo-pulse delayed by said delaying means with said reference signal.

16. An examined body interior information observing apparatus according to claim 15 wherein said time-analytical reflected light extracting means has a streak camera which the light having passed through said shutter means enters.

17. An examined body interior information observing apparatus according to claim 16 wherein detection sensitivity of said streak camera is controlled by said detection sensitivity varying means.

18. An examined body interior information observing apparatus according to claim 15 wherein said shutter means includes an optical shutter and a controlling apparatus controlling said optical shutter, said optical shutter being optically opened and closed by the application of a controlling signal output from said controlling apparatus, said controlling signal corresponding to an input of said reference signal to said controlling apparatus.

19. An examined body interior information observing apparatus according to claim 15 wherein said delaying means includes a photoelectric converting means for photoelectrically converting said second photo-pulse branched by said beam splitting means and an electric delaying device for delaying an output signal of said photoelectric converting means.

20. An examined body interior information observing apparatus according to claim 1 further comprising a scanning means for two-dimensionally scanning said photo-pulses radiated to said examined body.

21. An examined body interior information observing apparatus according to claim 1 further comprising a signal processing means processing the output signal of said time-analytical reflected light detecting means to produce a video signal.

22. An examined body interior information observing apparatus according to claim 21 further comprising a monitor means for displaying said video signal output from said signal processing means.

23. An examined body interior information observing apparatus according to claim 1 wherein said photo-pulse generating means includes a solid state laser emitting a laser light having a short pulse width.

24. An examined body interior information observing apparatus according to claim 1 wherein said photo-pulse generating means includes a solid state laser emitting a laser light having a short pulse width and a dye laser photo-excited by the laser light emitted from said solid state laser for emitting a laser light having a wide wavelength bandwidth.

25. An examined body interior information observing apparatus according to claim 1 further comprising at least one observing optical system for forming an optical image of said examined body.

26. An examined body interior information observing apparatus according to claim 25 further comprising a microscope having two said observing optical systems.

27. An examined body interior information observing apparatus according to claim 25 wherein said at least one observing optical system includes a relay lens system.

28. An examined body interior information observing apparatus according to claim 25 further comprising an illuminating optical system for illuminating said examined body with an illuminating light having a wavelength in a visible range.

29. An examined body interior information observing apparatus according to claim 28, further comprising an elongate insertable section, wherein said observing optical system and said illuminating optical system are provided at a tip of said elongate insertable section.

30. An examined body interior information observing apparatus according to claim 28, further comprising an endoscope wherein said observing optical system and said illuminating optical system are provided at a tip of an elongate insertable section of the endoscope.

31. An examined body interior information observing apparatus according to claim 30 wherein the thickness of said insertable part is small enough to be insertable into a blood vessel.

32. An examined body interior information observing apparatus according to claim 30 wherein said endoscope includes a channel, said photo-pulse generating means includes an elongate light guide for leading said photo-pulses emitted from said photo-pulse generating means, wherein said light guide is inserted through said channel and said photo-pulses radiated to a first end surface of said light guide are emitted to a side of said examined body from a second end surface of said light guide.

33. An examined body interior information observing apparatus according to claim 1 wherein said photo-pulse generating means includes an elongate light guide means for leading said photo-pulses emitted from said photo-pulse generating means to a first end surface of said light guide and emanating said photo-pulse from a second end surface of said light guide to said examined body.

34. An examined body interior information observing apparatus according to claim 33 wherein said light guide is formed of a fiber bundle in which respective optical fibers are cylindrically arranged and the photo-pulses are emitted in a radial direction of said cylinder from said second end surface and said photo-pulse generating means has a scanning means for successively radiating said photo-pulses to said first end surface of each said optical fiber.

35. An examined body interior information observing apparatus according to claim 34 wherein said light guide includes a single fiber bundle and has a driving means for two-dimensionally driving said second end surface of said single fiber bundle and two-dimensionally scanning the radiation position of said photo-pulses radiated to said examined body.

36. An examined body interior information observing apparatus according to claim 35 further comprising a signal processing means for processing the output signal of said time-analytical reflected light detecting means in the respective states driven by said driving means to produce a two-dimensional cross-sectioned image.

37. An examined body interior information observing apparatus according to claim 34 further comprising a signal processing means for processing the output signal of said time-analytical reflected light detecting means in the respective states scanned by said scanning means to produce a two-dimensional cross-sectioned image.

38. An examined body interior information observing apparatus according to claim 1 wherein said photo-pulse generating means includes an expanding means for expanding said photo-pulses emitted from said photo-pulse generating means and an optical fiber bundle transmitting the photo-pulses expanded by said expanding means and entering a first end surface of said fiber bundle, emitting the same to said examined body side from a second end surface of said fiber bundle, receiving on said second end surface the light reflected by said examined body and emitting the same to said time-analytical reflected light detecting means from said first end surface.

39. An examined body interior information observing apparatus according to claim 38 wherein said time-analytical reflected light detecting means includes an imaging device for receiving reflected light emitted through each optical fiber from said first end surface of said fiber bundle and converting the same to an electric signal.

40. An examined body interior information observing apparatus according to claim 39 further comprising a signal processing means for processing said electric signal output from said imaging device to produce a video signal corresponding to a cross-sectioned image of said interior of said examined body.

41. An examined body interior information observing apparatus according to claim 40 further comprising a monitor means for displaying said video signal.

42. An examined body interior information observing apparatus according to claim 39 wherein said time-analytical reflected light detecting means includes a reference pulse generating timing producing means for delaying said photo-pulses for a time corresponding to a light path length in which said photo-pulses emitted from said photo-pulse generating means and reflected at any depth in said examined body return to produce a reference pulse corresponding to said depth and a reflected light extracting means for extracting only a reflected light component substantially synchronized by said time-analytical reflected light detecting means with a time when said reference pulse in the light reflected by said examined body is output.

43. An examined body interior information observing apparatus according to claim 42 wherein said reference pulse generating timing producing means includes a signal processing means for processing said electric signal output from said imaging device when a output timing of said reference pulse is varied to produce a video signal corresponding to a three-dimensional cross-sectioned image.

44. An examined body interior information observing apparatus according to claims 38 or 39 further comprising a photo-shutter for controlling the passage/interception of the reflected light emitted from said first end surface of said optical fiber bundle.

45. An examined body interior information observing apparatus according to claim 38 wherein said time-analytical reflected light detecting means has a reference pulse generating timing producing means for delaying said photo-pulses for a time corresponding to a light path length in which said photo-pulses emitted from said photo-pulse generating means and reflected at any depth in said examined body return to produce a reference pulse corresponding to said depth and a reflected light extracting means for extracting only a reflected light component substantially synchronized by said time-analytical reflected light detecting means with a time when said reference pulse in the light reflected by said examined body is output.

46. An examined body interior information observing apparatus according to claim 1 further comprising a light transmitting means for radiating to said examined body said photo-pulses emitted from said photo-pulse generating means, and for leading light energy reflected by said examined body to said time-analytical reflected light detecting means, wherein said light transmitting means comprises an optical system divided into a means for memorizing only a reflected information signal corresponding to the reflected light energy reaching a surface of said optical system detected by said time-analytical reflected light detecting means, and an operating means for removing the reflected information signal memorized by said memorizing means from all information signals corresponding to all reflected light energy, including the light energy from said light transmitting means detected by said time-analytical reflected light detecting means and the returning light energy from an observed part of said examined body and producing the reflected information signal corresponding to a reflected light energy component actually reflected by said examined body.

47. An examined body interior information observing apparatus according to claim 1 wherein said photo-pulse generating means includes a solid state laser emitting a laser light having a short pulse width and a titanium sapphire laser photo-excited by the laser light emitted from said solid state laser for emitting a laser light having a wide wavelength bandwidth.

48. An examined body interior information observing apparatus comprising:
 a photo-pulse generating means for generating light energy in the form of photo-pulses for observing the interior of an examined body;
 a detecting timing setting means for delaying said photo-pulses generated by said photo-pulse generating means and producing a reference signal;
 a time-analytical reflected light energy detecting means for time-analytically detecting the light energy reflected within said examined body; and
 a detection sensitivity/detecting level varying means for varying a detection sensitivity/detecting level so that a level of at least an output signal of said time-analytical reflected light energy detecting means may vary.

49. An examined body interior information observing apparatus according to claim 48 wherein said detecting sensitivity/detecting level varying means includes means for variably-controlling said photo-pulse generating means.

50. An examined body interior information observing apparatus according to claim 48 wherein said detection sensitivity/detecting level varying means inputs into said time-analytical reflected light detecting means a detection sensitivity controlling signal for controlling a detection sensitivity of said time-analytical reflected light detecting means.

* * * * *

UNITED STATES PATENT AND TRADEMARK OFFICE
CERTIFICATE OF CORRECTION

PATENT NO. : 5,305,759
DATED : April 26, 1994
INVENTOR(S) : Mamoru Kaneko, et al.

It is certified that error appears in the above-indentified patent and that said Letters Patent is hereby corrected as shown below:

On the title page, item [30], the fourth inventor's last name should read --Takayama--.

Signed and Sealed this

Eleventh Day of October, 1994

Attest:

BRUCE LEHMAN

Attesting Officer

Commissioner of Patents and Trademarks